(12) United States Patent
Reed et al.

(10) Patent No.: US 10,878,935 B2
(45) Date of Patent: Dec. 29, 2020

(54) SYSTEMS AND METHODS FOR DETERMINING GENOTYPES FOR PERFORMING PHYSIOLOGICAL FUNCTIONS

(71) Applicant: WISCONSIN ALUMNI RESEARCH FOUNDATION, Madison, WI (US)

(72) Inventors: Jennifer L. Reed, Madison, WI (US); Christopher J. Tervo, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 784 days.

(21) Appl. No.: 14/950,131

(22) Filed: Nov. 24, 2015

(65) Prior Publication Data

US 2016/0147935 A1 May 26, 2016

Related U.S. Application Data

(60) Provisional application No. 62/083,573, filed on Nov. 24, 2014.

(51) Int. Cl.
*G16B 5/00* (2019.01)
(52) U.S. Cl.
CPC ..................................... *G16B 5/00* (2019.02)
(58) Field of Classification Search
None
See application file for complete search history.

(56) References Cited

PUBLICATIONS

Breitling, R., Vitkup, D. & Barrett, M. P. New surveyor tools for charting microbial metabolic maps. Nature Reviews Microbiology 6, 156-161 (2008).*
Dikicioglu, D., Pir, P. & Oliver, S. G. Predicting complex phenotype-genotype interactions to enable yeast engineering: *Saccharomyces cerevisiae* as a model organism and a cell factory. Biotechnology Journal 8, 1017-1034 (2013).*
Hubmann, G. et al. Quantitative trait analysis of yeast biodiversity yields novel gene tools for metabolic engineering. Metabolic Engineering 17, 68-81 (2013).*
Hubmann, G. et al. Identification of multiple interacting alleles conferring low glycerol and high ethanol yield in *Saccharomyces cerevisiae* ethanolic fermentation. Biotechnology for Biofuels 6, 1-17 (2013).*
Altschul et al., Basic Local Alignment Research Tool, J. Mol. Biol. (1990) 215, 403-410.
Aristidou et al., Modification of central metabolic pathway in *Escherichia coli* to reduce acetate accumulation by heterologous expression of the bacillus subtilis acetolactate synthase gene. Biotechnology and Bioengineering 44: 944-951, 1994.
Burgard et al., (2003) Optknock: A bilevel programming framework for identifying gene knockout strategies for microbial strain optimization. Biotechnology and Bioengineering 84: 647-657.
Burgard et al., (2004) Flux Coupling Analysis of Genome-Scale Metabolic Network Reconstructions. Genome Research 14: 301-312.
Choi et al., (2010) In Silico Identification of Gene Amplification Targets for Improvement of Lycopene Production. Applied and Environmental Microbiology 76: 3097-3105.
Cotten et al., (2013) Constraint-based strain design using continuous modifications (CosMos) of flux bounds finds new strategies for metabolic engineering. Biotechnology Journal 8: 595-604.
Curran et al., (2012) Expanding the chemical palate of cells by combining systems biology and metabolic engineering. Metabolic Engineering 14: 289-297.
Eiteman et al., (2006) Overcoming acetate in *Escherichia coli* recombinant protein fermentations. Trends in Biotechnology 24: 530-536.
Feist et al., (2010) Model-driven evaluation of the production potential for growth-coupled products of *Escherichia coli*. Metabolic Engineering 12: 173-186.
Fong et al., In silico design and adaptive evolution of *Escherichia coli* for production of lactic acid. Biotechnology and Bioengineering 91: 643-648. 2005.
Gawand et al., (2013) Novel approach to engineer strains for simultaneous sugar utilization. Metabolic Engineering 20: 63-72.
Hädicke et al., (2011) Computing complex metabolic intervention strategies using constrained minimal cut sets. Metabolic Engineering 13: 204-213.
Hamilton et al. (2012) Identification of Functional Differences in Metabolic Networks Using Comparative Genomics and Constraint-Based Models. PLoS One 7: e34670.
Jantama et al., (2008) Eliminating side products and increasing succinate yields in engineered strains of *Escherichia coli* C. Biotechnology and Bioengineering 101: 881-893.
Kim J, Reed JL, Maravelias CT (2011) Large-Scale Bi-Level Strain Design Approaches and Mixed-Integer Programming Solution Techniques. PLoS One 6: e24162.
Kim et al. (2010) OptORF: Optimal metabolic and regulatory perturbations for metabolic engineering of microbial strains. BMC Systems Biology 4: 53.
Lee et al., (2012) Systems metabolic engineering of microorganisms for natural and non-natural chemicals. Nat. Chem. Biol. 8: 536-546.
Lian et al., (2014) Metabolic engineering of a *Saccharomyces cerevisiae* strain capable of simultaneously utilizing glucose and galactose to produce enantiopure (2R,3R)-butanediol. Metabolic Engineering 23: 92-99.
Lin et al., (2005) Metabolic engineering of aerobic succinate production systems in *Escherichia coli* to improve process productivity and achieve the maximum theoretical succinate yield. Metabolic Engineering 7: 116-127.
Lun et al., (2009) Large-scale identification of genetic design strategies using local search. Molecular Systems Biology 5.
Ohno et al., (2013) FastPros: Screening of reaction knockout strategies for metabolic engineering. Bioinformatics.

(Continued)

*Primary Examiner* — Soren Harward
(74) *Attorney, Agent, or Firm* — Daniel A. Blasiole; DeWitt LLP

(57) ABSTRACT

Systems and methods for determining genetic variations of an organism for performing a physiological function. The systems include a number of modules that can be integrated into existing metabolic engineering algorithms. The methods include use of the modules. The physiological function may include growth, compound production, and/or metabolic reaction flux, among others.

18 Claims, 19 Drawing Sheets

(56) References Cited

PUBLICATIONS

Olins et al., A Novel Sequence Element Derived from Bacteriophage T7 mRNA Acts as an Enhancer of Translation of the lacZ Gene in *Escherichia coli*, The Journal of Biological Chemistry, vol. 264, No. 29, pp. 16973-16976 1989.

Orth et al., (2010) What is flux balance analysis? Nat Biotech 28: 245-248.

Orth et al., (2011) A comprehensive genome-scale reconstruction of *Escherichia coli* metabolism—2011. Mol Syst Biol 7.

Patil et al., (2005) Evolutionary programming as a platform for in silico metabolic engineering. BMC Bioinformatics 6: 308.

Pharkya et al., (2004) OptStrain: A computational framework for redesign of microbial production systems. Genome Research 14: 2367-2376.

Pharkya et al., (2006) An optimization framework for identifying reaction activation/inhibition or elimination candidates for overproduction in microbial systems. Metabolic Engineering 8: 1-13.

Ranganathan et al., (2010) OptForce: An Optimization Procedure for Identifying All Genetic Manipulations Leading to Targeted Overproductions. PLoS Comput Biol 6: e1000744.

Reed et al., 2006, Towards multidimensional genome annotation, Nature Reviews Genetics, 7(2):130-141.

Sánchez et al., (2005) Novel pathway engineering design of the anaerobic central metabolic pathway in *Escherichia coli* to increase succinate yield and productivity. Metabolic Engineering 7: 229-239.

Tepper et al., (2010) Predicting metabolic engineering knockout strategies for chemical production: accounting for competing pathways. Bioinformatics 26: 536-543.

Tervo et al., (2012) FOCAL: an experimental design tool for systematizing metabolic discoveries and model development. Genome Biology 13: R116.

Tervo et al., Expanding Metabolic Engineering Algorithms Using Feasible Space and Shadow Price Constraint Modules. Metab Eng Commun. Dec. 1, 2014;1:1-11.

Trinh et al., (2008) Minimal *Escherichia coli* Cell for the Most Efficient Production of Ethanol from Hexoses and Pentoses. Applied and Environmental Microbiology 74: 3634-3643.

Vadali et al., (2005) Enhanced Lycopene Productivity by Manipulation of Carbon Flow to Isopentenyl Diphosphate in *Escherichia coli*. Biotechnology Progress 21: 1558-1561.

Von Kamp et al., (2014) Enumeration of Smallest Intervention Strategies in Genome-Scale Metabolic Networks. PLoS Comput Biol 10: e1003378.

Yang et al., (2011) EMILiO: A fast algorithm for genome-scale strain design. Metabolic Engineering 13: 272-281.

Yim et al., (2011) Metabolic engineering of *Escherichia coli* for direct production of 1,4-butanediol. Nat Chem Biol 7: 445-452.

Zha et al., (2009) Improving cellular malonyl-CoA level in *Escherichia coli* via metabolic engineering. Metabolic Engineering 11: 192-198.

Zomorrodi et al., (2012) Mathematical optimization applications in metabolic networks. Metabolic Engineering 14: 672-686.

\* cited by examiner

*Metabolic Engineering Objective — Gene Deletion Penalties*

*maximize*
*subject to:*

*Cellular Growth*
    *maximize*
    *subject to:*
        steady-state mass balance
        enzyme capacity
        thermodynamics
        reaction deletions

*Module Objectives*    Eq. 5.4, 5.15
    *max/min*
    *subject to:*
        module constraints    Eq. 5.5–5.13, 5.16–5.20
        reaction deletions    Eq. 5.11–5.12, 5.17–5.18

⎫ Multiple Modules
⎬ may be used
⎭ simultaneously

Eq. 5.14, 5.22–5.25 module acceptance criteria
GPR association constraints
gene deletions
gene deletion constraints

FIG. 1

Coupling Module - Weak Coupling Only

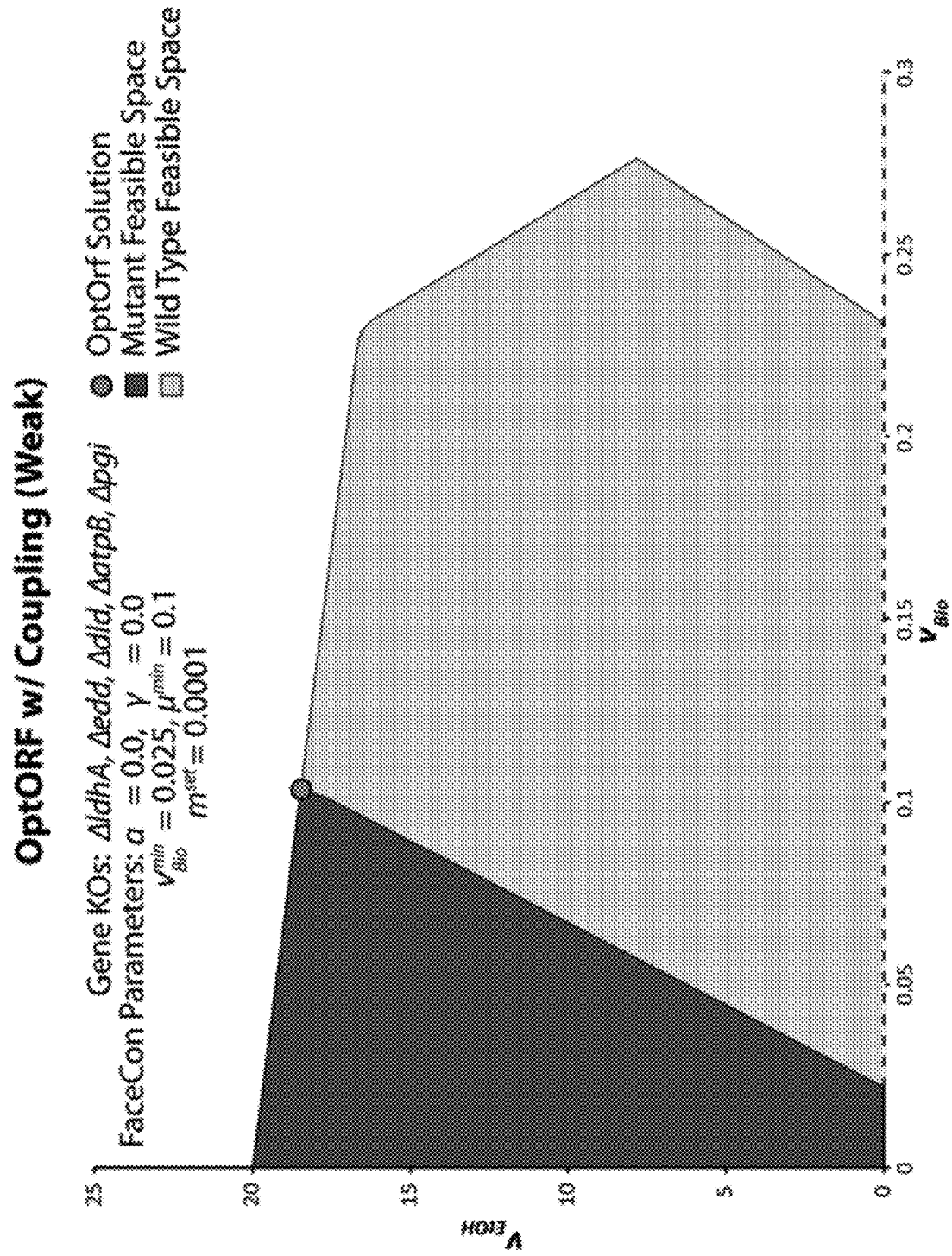

SYSTEMS AND METHODS FOR DETERMINING GENOTYPES FOR PERFORMING PHYSIOLOGICAL FUNCTIONS

STATEMENT REGARDING FEDERALLY SPONSORED RESEARCH

This invention was made with government support under 1053712 awarded by the National Science Foundation. The government has certain rights in the invention.

FIELD OF THE INVENTION

This invention is directed to systems and methods for genetically designing cells such as microorganisms for performing specific physiological functions.

BACKGROUND

Genome-scale models (GEMS) are powerful tools allowing for the prediction of cellular growth, flux profiles, and mutant strain phenotypes [1]. Over the last decade, with the development of new computational algorithms, GEMS have been used to guide the design of strains for biochemical production, such as biofuels and commodity chemicals (reviewed in [2, 3, 4]). While GEMs are valuable tools, new computational algorithms are still needed to evaluate them and apply them in new ways.

Many strain design algorithms exist that identify which network modifications are needed to improve chemical production. These modifications can involve reaction deletions (OptKnock), metabolic or regulatory gene deletions (OptGene and OptORF), reaction additions (OptStrain and SimOptStrain), or flux increases/decreases (OptReg, OptForce, CosMos, FSEOF) [3, 5, 6, 7, 8, 9, 10, 11, 12, 13]. The bi-level optimization approaches used to identify these modifications can be computationally expensive and recent efforts have improved their run-time performances [9, 13, 14, 15, 16]. Many of these metabolic engineering algorithms focus on improving the desired chemical production when the proposed mutant is operating at its maximal growth rate. By coupling chemical production to growth, selection for growth rate using a chemostat or sequential batch cultures can enrich for strains with increased chemical production [17]. One such algorithm, OptORF, is used extensively in this work [5]. The OptORF algorithm extends upon OptKnock by using gene rather than reaction deletions as potential modifications. By accounting for gene and transcriptional regulatory network information, OptORF proposes deleting or overexpressing metabolic or regulatory genes (as opposed to reaction level deletions proposed by OptKnock) to increase chemical production. By doing this, OptORF avoids designs that would be impossible to implement, due to genetic interactions between reactions or regulatory effects.

While metabolic engineering methods have been successful [2, 8, 17, 18], most of these approaches cannot consider the ramifications of undesirable suboptimal flux distributions (e.g. production with low productivity) [9, 19, 20, 21, 22], or production phenotypes at or near stationary phase in batch cultures. Additionally, these algorithms are limited in their ability to tailor a strain's behavior to address more complex problems (e.g., the co-utilization of multiple substrates [23, 24, 25] or elimination of undesirable by-products [26, 27, 28, 29]). Consequently, while these approaches are valuable in designing adaptive evolutionary strains based on single criteria (e.g., high production at maximal growth rates), they often lack the ability to efficiently propose strains meeting multiple design criteria that are of interest to investigators. To address these problems in small networks, techniques such as constrained minimal cut sets [30] can be used to allow researchers to meet additional design criteria (e.g., elimination of undesired by-products) without affecting the desired chemical production phenotype. Recent advances allow enumeration of the smallest minimal cut sets in genome-scale networks, from which constrained minimal cut sets can be identified [31]. However, all minimal cut sets can still not be enumerated for genome-scale networks, and the smallest minimal cut sets identified first might not correspond to constrained minimal cut sets meeting additional design criteria. Additionally, strategies for finding constrained minimal cut sets that consider transcriptional regulation, media selection or degree of coupling between biomass and chemical production have not been developed.

Previously, the forced coupling algorithm (FOCAL) was developed to identify conditions (e.g., gene deletions or media conditions) that ensure directional coupling between two fluxes (flux through $v_x$ implies flux through $v_y$) [32]. By changing media conditions or deleting genes, FOCAL affects the shape of the resulting feasible solution space. FOCAL was shown to be used in the design of a mutant strain that must co-utilize xylose and glucose simultaneously in order to grow. While the modifications were interesting, they did not work to increase the overall productivity of the organism since no metabolic engineering objective was included. Moreover, this approach could only enforce directional coupling between fluxes which is often an overly stringent condition for metabolic engineering strain designs.

Recently, Ohno et al. used shadow prices from flux balance analysis (FBA) solutions to guide a greedy algorithm for increasing chemical productivity as reaction deletions are added [14]. Double deletion mutants with the top desired shadow prices (which indicate the rate of change in growth divided by the rate of change in chemical production) were used as "parent" strains to find triple deletion knockouts with the best shadow prices. This greedy search process, called FastPros, was repeated for up to 25 knockouts, and for each iterative screening step, any sets of deletions which resulted in a non-negative shadow prices (indicating coupling between growth and chemical production) were stored as candidates for further analysis and excluded from further screening. The authors then used OptKnock to maximize chemical production using only the stored reaction knockouts found by their FastPros process. Because they use a greedy algorithm, their method does not guarantee that the set of knockouts with the highest shadow prices are discovered. Additionally, since the authors use OptKnock to propose strain designs, their approach does not control or optimize the degree of coupling between chemical production and cellular growth when mutants are proposed.

Systems and methods that address the above-mentioned problems are needed.

SUMMARY OF THE INVENTION

The present invention is directed to modules for controlling the shape of an organism's feasible space. Exemplary modules are referred to as "Feasible Space Constraint" (FaceCon) and "Shadow Constraint" (ShadowCon) modules. These modules allow many additional types of design criteria to be considered besides directional coupling. These modules can be easily added to mixed integer linear adaptive evolution metabolic engineering algorithms to incorporate additional design criteria, while retaining the original objective of the method (e.g., coupling growth to chemical production or enzyme activity). Since there are often many possible solutions to these strain design algorithms, embedding these modules allows only the subset of those mutants to be found if the criteria associated with these modules is met. Such filtering is needed as models become larger and the computational cost (i.e., CPU time) of generating numerous strain designs increases, due to the combinatorial explosion associated with increasing numbers of integer variables and integer cuts needed to find alternate solutions. To date, the only type of filtering that can be done works to prevent finding solutions that have large ranges of chemical production at the maximum growth rate [19, 33].

FaceCon modules are included as additional inner optimization problems and ensure that any proposed mutant cannot operate within a user-defined region (i.e., no feasible flux distribution can exist within a user-defined region). By defining this excluded region, various feasible space characteristics can be enforced. Below we describe three types of FaceCon modules:

1. Coupling Module: This module allows a researcher to enforce different types of coupling (directional or weak) between a flux of interest ($v_y$) and another flux ($v_x$) depending on the formulation and parameter selection. This module can be used to find mutants with directional coupling (i.e., flux through $v_x$ implies flux through $v_y$ for all values of $v_x$ [34]) or weak coupling (where flux through $v_x$ implies flux for $v_y$ only for some positive values of $v_x$). Depending on how the coupling module is implemented one can require mutants have directional coupling, weak coupling, or either directional or weak coupling. The result of any of these implementations is that a defined portion of the $v_x$ axis is excluded from the solution space of a proposed mutant.
2. Chemical Level Module: The chemical level module ensures proposed mutants meet criteria associated with the production level of a chemical of interest, $v_y$ (e.g., a desired product or undesired by-product). This module finds mutants whose solution space excludes solutions with $v_y$ below (or above) a user-defined threshold ($\beta$) within a defined region (e.g., $v_y$ must be greater than $\beta$ when $v_x$ is greater than $v^{min}$).
3. Direct Constraint Module: This module is the most comprehensive and with proper parameter selection can encompass the functions of the two previous FaceCon modules. This module allows the user to define a particular region that must be excluded from the solution space of any proposed mutant; thus, the researcher is able to directly influence the solution space of any mutant proposed by a metabolic engineering algorithm.

ShadowCon modules are also included as inner optimization problems and can be used to control or optimize the degree of coupling between a flux of interest ($v_y$) and another flux ($v_x$) once coupling between two fluxes occurs.

More generally, the invention provides a computer-implemented method for determining genetic variations of an organism for performing a physiological function wherein the physiological function corresponds to an objective function in a network map of the organism. The method comprises determining, from a set of possible genotypes corresponding to a range of rates of flux through a first reaction and a range of rates of flux through a second reaction, a subset of possible genotypes that affects an objective function so that a non-zero rate of flux through the second reaction implies a non-zero rate of flux through the first reaction if the non-zero rate of flux through the second reaction is greater than a user-defined value, wherein the non-zero rate of flux through the second reaction does not imply a non-zero rate of flux through the first reaction if the non-zero rate of flux through the second reaction is less than the user-defined value.

The method additionally or alternatively comprises determining, from a set of possible genotypes corresponding to a range of rates of flux through a third reaction and a range of rates of flux through a fourth reaction, a subset of possible genotypes that affects an objective function so that each rate of flux through the third reaction is greater than a user-defined value when the rate of flux through the fourth reaction is greater than a user-defined value.

The method additionally or alternatively comprises determining, from a set of possible genotypes corresponding to a range of rates of flux through a fifth reaction and a range of rates of flux through a sixth reaction, a subset of possible genotypes that affects an objective function so that each rate of flux through the fifth reaction is less than a user-defined value when the rate of flux through the sixth reaction is greater than a user-defined value.

The method additionally or alternatively comprises determining, from a set of possible genotypes corresponding to a range of rates of flux through a seventh reaction and a range of rates of flux through an eighth reaction, a subset of possible genotypes that affects an objective function so that a ratio of a change of rate of flux through the seventh reaction per a change of rate of flux through the eighth reaction is greater than a user-defined ratio of a change of rate of flux through the seventh reaction per a change of rate of flux through the eighth reaction at rates of flux through the eighth reaction greater than a user-defined value.

The method additionally or alternatively comprises determining, from a set of possible genotypes corresponding to a range of rates of flux through a ninth reaction and a range of rates of flux through a tenth reaction, a subset of possible genotypes that affects an objective function so that a ratio of a change of rate of flux through the ninth reaction per a change of rate of flux through the tenth reaction is less than a user-defined ratio of a change of rate of flux through the ninth reaction per a change of rate of flux through the tenth reaction at rates of flux through the tenth reaction greater than a user-defined value.

The method additionally or alternatively comprises determining, from a set of possible genotypes corresponding to a range of rates of flux through an eleventh reaction and a range of rates of flux through a twelfth reaction, a subset of possible genotypes that affects an objective function so that the ratio of a change of rate of flux through the eleventh reaction per a change of rate of maximal flux through the twelfth reaction is between user-specified values or is maximized or minimized.

A reaction selected from the group consisting of the first reaction, the third reaction, the seventh reaction, and the eleventh reaction is preferably selected from the group consisting of extracellular production of a desired compound and a desired enzyme activity.

A reaction selected from the group consisting of the fifth reaction and the ninth reaction is preferably selected from the group consisting of extracellular production of an undesired compound and undesired enzyme activity.

A reaction selected from the group consisting of the second reaction, the fourth reaction, the sixth reaction, the eighth reaction, the tenth reaction, and the twelfth reaction preferably comprises biomass production.

A reaction selected from two or more of the group consisting of the first reaction, the third reaction, the seventh reaction, and the eleventh reaction may comprise extracellular production of a same compound or same enzyme activity.

The invention also provides a computer-implemented system for determining genetic variations of an organism for performing a physiological function, wherein the physiological function corresponds to an objective function in a network map of the organism.

The system comprises a first module configured to determine, in a set of possible genotypes corresponding to a range of rates of flux through a first reaction and a range of rates of flux through a second reaction, a subset of possible genotypes that affects an objective function so that a non-zero rate of flux through the second reaction implies a non-zero rate of flux through the first reaction if the non-zero rate of flux through the second reaction is greater than a user-defined value, wherein the non-zero rate of flux through the second reaction does not imply a non-zero rate of flux through the first reaction if the non-zero rate of flux through the second reaction is less than the user-defined value.

The system additionally or alternatively comprises a second module configured to determine, in a set of possible genotypes corresponding to a range of rates of flux through a third reaction and a range of rates of flux through a fourth reaction, a subset of possible genotypes that affects an objective function so that each rate of flux through the third reaction is greater than a user-defined value when the rate of flux through the fourth reaction is greater than a user-defined value.

The system additionally or alternatively comprises a third module configured to determine, in a set of possible genotypes corresponding to a range of rates of flux through a fifth reaction and a range of rates of flux through a sixth reaction, a subset of possible genotypes that affects an objective function so that each rate of flux through the fifth reaction is less than a user-defined value when the rate of flux through the sixth reaction is greater than a user-defined value.

The system additionally or alternatively comprises a fourth module configured to determine, in a set of possible genotypes corresponding to a range of rates of flux through a seventh reaction and a range of rates of flux through an eighth reaction, a subset of possible genotypes that affects an objective function so that a ratio of a change of rate of flux through the seventh reaction per a change of rate of flux through the eighth reaction is greater than a user-defined ratio of a change of rate of flux through the seventh reaction per a change of rate of flux through the eighth reaction at rates of flux through the eighth reaction greater than a user-defined value.

The system additionally or alternatively comprises a fifth module configured to determine, in a set of possible genotypes corresponding to a range of rates of flux through a ninth reaction and a range of rates of flux through a tenth reaction, a subset of possible genotypes that affects an objective function so that a ratio of a change of rate of flux through the ninth reaction per a change of rate of flux through the tenth reaction is less than a user-defined ratio of a change of rate of flux through the ninth reaction per a change of rate of flux through the tenth reaction at rates of flux through the tenth reaction greater than a user-defined value.

The system additionally or alternatively comprises a sixth module configured to determine, in a set of possible genotypes corresponding to a range of rates of flux through an eleventh reaction and a range of rates of flux through a twelfth reaction, a subset of possible genotypes that affects an objective function so that the ratio of a change of rate of flux through the eleventh reaction per a change of rate of maximal flux through the twelfth reaction is between user-specified values or is optimized.

The second and third modules preferably comprise a single module. The fourth and fifth modules also preferably comprise a single module.

Exemplary versions of the first, second, third, fourth, and fifth modules include the FaceCon modules described herein.

An exemplary version of the sixth module is the ShadowCon module described herein.

A module selected from the group consist of the first module, the second module, the third module, the fourth module, the fifth module, and the sixth module is preferably configured to add a mixed-integer linear program subproblem to a metabolic engineering algorithm.

The invention also provides a method of generating a cell capable of performing a physiological function. The method comprises determining a subset of possible genotypes that affects an objective function as described above and generating a cell having one of the possible genotypes in the subset. The physiological function is preferably selected from the group consisting of increased or decreased production of a compound and increased or decreased enzyme activity. A reaction selected from the group consisting of the first reaction, the third reaction, the seventh reaction, and the eleventh reaction comprises increased production of the compound or an increase in the enzyme activity. The cell is preferably a microorganism.

The invention also provides a method of producing a compound. The method comprises culturing the cell capable of performing a physiological function as described above and isolating the compound.

The invention also provides a method of improving an enzyme's metabolic activity. The method comprises culturing the cell capable of performing a physiological function comprising increased or decreased activity of one or more enzymes.

The invention also provides a method of producing an enzyme. The method comprises culturing the cell capable of performing a physiological function comprising increased activity of one or more enzymes and isolating the one or more enzymes.

In some versions, the cell is a population of cells that undergo adaptive evolution to achieve the desired physiological function. The adaptive evolution selects for cells with increased or decreased production of a compound and increased or decreased enzyme activity. Adaptive evolution may be performed by culturing the cells iteratively over several generations through multiple aliquots of media having an increase or decrease in one or more medium components with respect to a standard medium. The magnitude of the increase or decrease in the one or more medium components may itself increase or decrease over the course of the iterative aliquot culturing.

The invention also provides microorganisms configured for producing ethanol. The microorganisms comprising a modification that functionally deletes gene products of a set of genes. The set of genes are selected from the group consisting of tpiA and a gene selected from atpA, atpB, atpC, aptD, atpE, atpF, atpG, and atpH or homologs thereof; a gene selected from tesB, mgsA, glcA, lldP, tpiA, and a gene selected from atpA, atpB, atpC, aptD, atpE, atpF, atpG, and atpH or homologs thereof; tesB, mgsA, dld, ldhA, tpiA, and a gene selected from atpA, atpB, atpC, aptD, atpE, atpF, atpG, and atpH or homologs thereof; glcA, lldP, pgi, and a gene selected from atpA, atpB, atpC, aptD, atpE, atpF, atpG, and atpH or homologs thereof; dld, ldhA, pgi, and a gene selected from atpA, atpB, atpC, aptD, atpE, atpF, atpG, and atpH or homologs thereof; gdhA, glcA, lldp, and a gene selected from atpA, atpB, atpC, aptD, atpE, atpF, atpG, and atpH or homologs thereof; gdhA, dld, ldhA, and a gene selected from atpA, atpB, atpC, aptD, atpE, atpF, atpG, and atpH or homologs thereof; glcA, lldP, and a gene selected from atpA, atpB, atpC, aptD, atpE, atpF, atpG, and atpH or homologs thereof; dld, ldhA, and a gene selected from atpA, atpB, atpC, aptD, atpE, atpF, atpG, and atpH or homologs thereof; ldhA, edd, dld, pgi, and a gene selected from atpA, atpB, atpC, aptD, atpE, atpF, atpG, and atpH or homologs thereof; focA, focB, glcA, and lldp or homologs thereof; focA, focB, dld, and ldhA or homologs thereof; focA, focB, glcA, lldP, and ppc or homologs thereof; focA, focB, dld, ldhA, and ppc or homologs thereof; glcA, lldP, a gene selected from ptsH, ptsI, ptsG, and crr, and a gene selected from atpA, atpB, atpC, aptD, atpE, atpF, atpG, and atpH or homologs thereof; dld, ldhA, a gene selected from ptsH, ptsI, ptsG, and crr, and a gene selected from atpA, atpB, atpC, aptD, atpE, atpF, atpG, and atpH or homologs thereof; ydbK, gdhA, tpiA, and ppc or homologs thereof; tpiA, fpr, and ppc or homologs thereof; glcA, lldP, ppc, and a gene selected from atpA, atpB, atpC, aptD, atpE, atpF, atpG, and atpH or homologs thereof; dld, ldhA, ppc, and a gene selected from atpA, atpB, atpC, aptD, atpE, atpF, atpG, and atpH or homologs thereof; and mgsA, gadA, gdhA, edd, gnd, glcB, aceB, tpiA, and a gene selected from sucA and sucB. The modification preferably comprises a genetic deletion of the set of genes. The microorganism is preferably *E. coli*.

The objects and advantages of the invention will appear more fully from the following detailed description of the preferred embodiment of the invention made in conjunction with the accompanying drawings.

BRIEF DESCRIPTION OF THE DRAWINGS

FIG. 1. Modules added as inner problems to extend existing metabolic engineering algorithms. FIG. 1 demonstrates how FaceCon and ShadowCon modules are implemented within a metabolic engineering algorithm, in this example OptORF. All module variables (including fluxes) are completely independent of the metabolic engineering variables, with the exception of reaction deletions which are shared across all subproblems. By being modular, these constraints can be added to most flux balance analysis (FBA)-centric bi-level approaches and can be mixed and matched to include addition strain design criteria.

FIG. 3 depicts a Venn diagram of the set of constraints and parameter values that are used in a given FaceCon module. Many modules are subsets of the more comprehensive Direct Constraint module. The Direct Constraint parameter values are provided to reproduce the functionality of each of the other FaceCon modules.

FIGS. 4A-C show the effects of the coupling (FIG. 4A), chemical level (FIG. 4B) and direct topology (FIG. 4C) modules to illustrate each module's intent and capabilities. The dot ("Module Solution") indicates the optimal solution that would be found from including each module in OptORF. The dashed lines and hatched regions indicate the excluded regions imposed by the FaceCon modules.

FIGS. 5A-7C. Illustrative examples of FaceCon modules used in conjunction with OptORF. FIGS. 5A-B depict results of a coupling module added to guarantee that weak coupling would occur but not directional coupling. FIG. 5A shows a schema of a hypothetical network map with the solutions proposed by the module. FIG. 5B shows $v_{10}$ versus $v_{Bio}$. The dashed line on the x-axis in FIG. 5B indicates where the excluded region begins. FIG. 6A shows a schema of a hypothetical network map with the solutions proposed by the module. FIG. 6B shows $v_{10}$ versus $v_{Bio}$. FIG. 6C shows $v_{12}$ versus $v_{Bio}$. The hatched region in FIG. 6C indicates the excluded region imposed by the module. FIGS. 7A-7C shows results of a direct constraint module added to force the co-production of $E_{ex}$ and $I_{ex}$ for large growth rates. FIG. 7A shows a schema of a hypothetical network map with the solutions proposed by the module. FIG. 7B shows $v_{10}$ versus $v_{Bio}$. FIG. 7C shows $v_{12}$ versus $v_{Bio}$. For each of FIGS. 5A, 6A, and 7A, x's on the network map indicate a reaction knockout. For each of FIGS. 5B, 6B, and 7B, the dotted vertical lines show the $\mu^{min}$ and $v^{min}$ values used in OptORF and FaceCon modules, respectively.

FIGS. 8A-D show results from OptORF including the following FaceCon modules: No FaceCon modules (FIG. 8A), Coupling module (only directional coupling) (FIG. 8B), Coupling module (only weak coupling) (FIG. 8C), and Direct Topology module (FIG. 8D). Parameters used in FaceCon modules for each case are provided above the mutant feasible regions. Dashed lines and hatched regions indicate excluded regions imposed by the FaceCon modules. OptORF without any modules (FIG. 8A) finds a lower chemical production phenotype compared to OptORF with the Coupling module (FIGS. 8B and 8C) due to gene deletion penalties used in OptORF. Additionally, no tilt was applied to the OptORF algorithm resulting in a strain design where there is no coupling between biomass and ethanol production. Alternate solutions exist, and replacing the glcA and lldP deletions with dld and ldhA deletions has a negligible effect on the feasible regions shown in FIGS. 8B-8D.

FIGS. 9A-C. FaceCon examples using "tilted" OptORF. FaceCon filtering examples were generated using OptORF with a "tilted" objective function. FIG. 9A shows results from OptORF without any FaceCon modules. FIG. 9B shows results from OptORF with the Coupling module (weak coupling). FIG. 9C shows results from OptORF with the Coupling module (weak coupling only). As can be seen, the method is still capable of filtering the many possible solutions that couple ethanol production to cellular growth.

FIG. 10A shows $v_{EtOH}$ versus $v_{Bio}$. FIG. 10B shows $v_{Formate}$ versus $v_{Bio}$. Hatched area indicates infeasible region. Results generated using OptORF with a "tilted" objective.

DETAILED DESCRIPTION OF THE INVENTION

Figure 2:
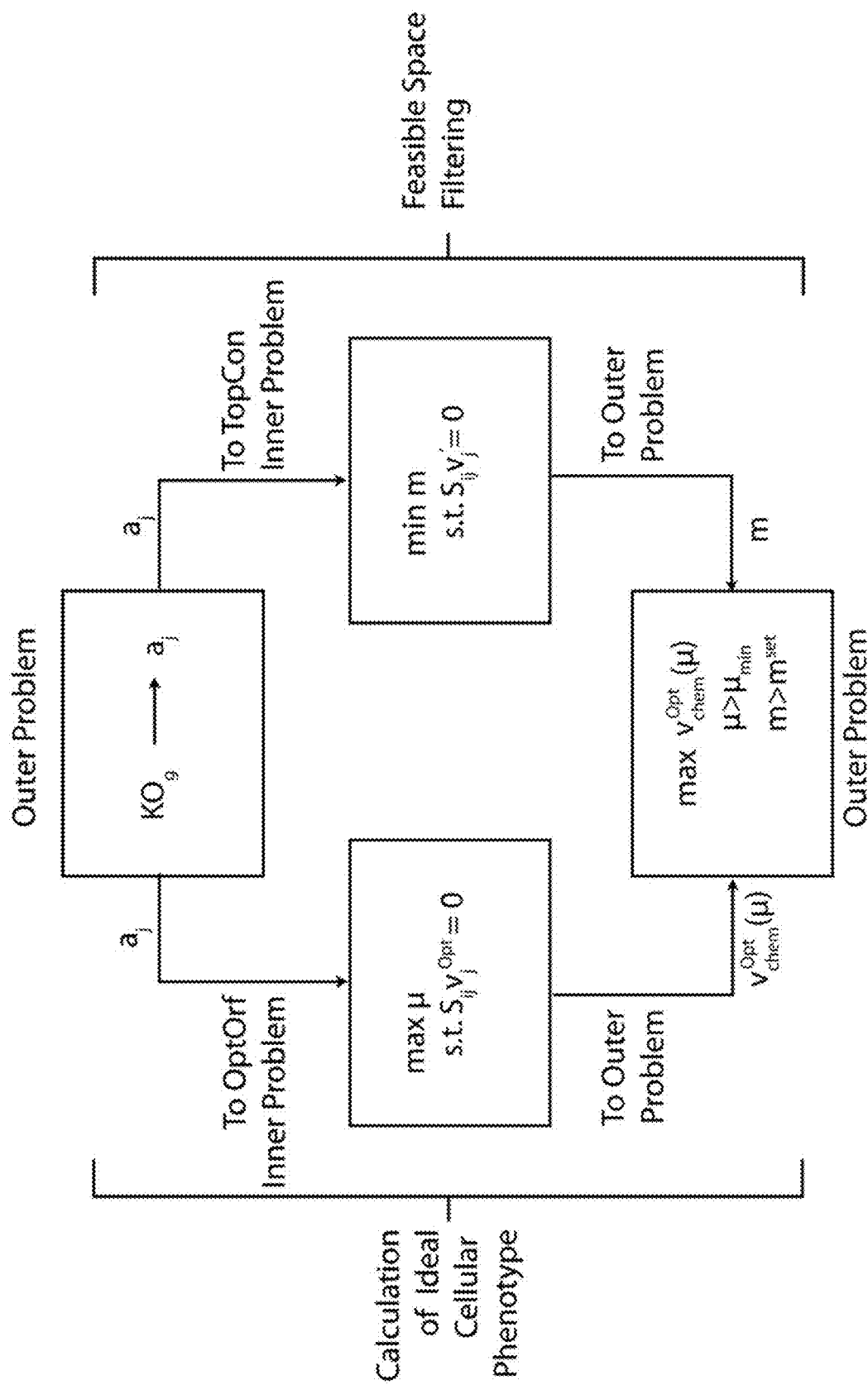
FIG. 2. Information Flow in OptORF+FaceCon. When using FaceCon or ShadowCon in conjunction with a metabolic engineering algorithm, the subproblems are independent of one another and share no variables except for knockout information encoded in the integer variable, aj, which is determined by the outer problem. On the left, OptORF works to maximize chemical production (outer problem) for a cell performing at maximal growth rate, μ. This problem uses variables $v^{opt}$ to determine the relevant fluxes. On the right-hand side, FaceCon uses the same knockout information to evaluate the feasible space of the proposed mutant using a different set of flux variables, v'. The slope, based on user-parameters, is fed to the outer problem to determine feasibility. Using a FaceCon module does not increase the number of integer variables used to solve the problem so that complexity should scale in a polynomial fashion with the increased size of the problem.

Methods and systems for analyzing steady-state in silico models of biological networks are provided herein. A steady-state model can be used to simulate different aspects of cellular behavior of cells under different environmental and genetic conditions, thereby providing valuable information for a range of industrial and research applications. Developing steady-state models of biological networks can be used to inform and guide the research process, potentially leading to the identification and production of new enzymes, medicines or metabolites of commercial importance.

As used herein, the term "concentration" refers to a numerical value with physical units of mass*volume$^{-1}$, such as molar and millimolar. Such quantities include but are not limited to molecules in a biochemical network, such as glucose, pyruvate, lactate, enzymes that carry out biochemical transformations or transport reactions such as hexokinase, adenosine deaminase, and sodium-potassium ATPase pump.

As used herein, the term "mass balance" refers to a linear algebraic equation with respect to time which equates the net production rate and net consumption rate for each component in a specified biological network.

As used herein the term "flux" or "reaction flux" refers to a single flux in a flux distribution. Individual fluxes can be represented as the difference between a forward and reverse flux, with units mass, or number of moles, or number of molecules per unit biomass per unit time.

As used herein, the term "flux distribution" refers to a directional, quantitative list of values corresponding to the set of reactions in a network, representing the mass flow per unit biomass per unit time for each reaction in the network being analyzed.

As used herein, the term "biological network" refers to assembled reactions reflecting biological processes. Examples of biological networks include but are not limited to metabolic networks, signaling networks, and regulatory networks.

As used herein, the term "network map" refers to the set of reactions in the biological network and the compounds, macromolecules, and/or genes they are associated with.

As used herein, the term "stoichiometric matrix" or "S" refers to a matrix with the stoichiometric coefficients for reactions represented by the columns and the substrates and products in the rows. The stoichiometric matrix may be written for any biological network. Examples include, but are not limited to, metabolic networks and signaling networks.

As used herein, the term "steady state" refers to any of a number of conditions for which the flux distribution and concentrations do not change over time. Equilibrium is a special case which also satisfies the steady-state. In general, unless otherwise specified, references to the steady state imply a non-equilibrium steady state.

The reconstruction of a genome-scale reaction network (network map) requires the identification of all its chemical components and the chemical transformations that they participate in. This process primarily relies on annotated genomes and detailed bibliomic assessment. See Reed, et al. (2006), *Nature Reviews Genetics*, 7(2):130-141, which is hereby incorporated by reference in its entirety. See also, U.S. Pat. No. 8,301,393 which is also incorporated by reference in its entirety. The result of this process is the stoichiometric matrix, S, that is used in mass balances $$S \cdot v = 0$$

that are the basis of all steady-state models. Here v is the vector of the reaction fluxes (i.e., flux distribution). All biochemical transformations are fundamentally uni- or bi-molecular and their reaction rates can be represented by mass action kinetics, or generalizations thereof. The net reaction flux for every reaction in a network can be represented by the difference between a forward and reverse flux. This commonly used formulation is based on several well-known assumptions, such as constant temperature, volume, and homogeneity of the medium. A steady-state flux distribution (v) must satisfy the mass balances.

The availability of genomic and bibliomic data can be used to define S, which has been described in detail. S is primarily derived from an annotated genomic sequence fortified with any direct bibliomic data on the organisms' gene products. In the physico-chemical context, S represents chemistry (i.e. stoichiometry of reactions). In the biological and genetic considerations context, the matrix S is reconstructed based on the content of a genome and is a property of a species. As used herein, the term "reaction" is intended to mean a conversion that consumes a substrate or forms a product that occurs in a biological network. The term can include a conversion that occurs due to the activity of one or more enzymes that are genetically encoded by an organism's genome. The term can also include a conversion that occurs spontaneously. Conversions included in the term include, for example, changes in chemical composition such as those due to nucleophilic or electrophilic addition, nucleophilic or electrophilic substitution, elimination, isomerization, deamination, phosphorylation, methylation, glycosylation, reduction, oxidation or changes in location such as those that occur due to a transport reaction that moves one or more reactants within the same compartment or from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "reactant" is intended to mean a chemical that is a substrate or a product of a reaction that occurs in a biological network. The term can include substrates or products of reactions performed by one or more enzymes encoded by gene(s), reactions occurring in cells that are performed by one or more non-genetically encoded macromolecule, protein or enzyme, or reactions that occur spontaneously in a cell. Metabolites are understood to be reactants within the meaning of the term. It will be understood that when used in reference to an in silico model or data structure, a reactant is intended to be a representation of a chemical that is a substrate or a product of a reaction that occurs in a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more substrates and the number of one or more products in a chemical reaction. Typically, the numbers are integers as they denote the number of molecules of each reactant in an elementally balanced chemical reaction that describes the corresponding conversion. However, in some cases the numbers can take on non-integer values, for example, when used in a lumped reaction or to reflect empirical data.

As used herein, the term "plurality," when used in reference to reactions or reactants is intended to mean at least 2 reactions or reactants. The term can include any number of reactions or reactants in the range from 2 to the number of naturally occurring reactants or reactions for a particular cell. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell such as at least 20%, 30%, 50%, 60%, 75%, 90%, 95% or 98% of the total number of naturally occurring reactions that occur in the particular cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, a stoichiometric coefficient, or a rate constant.

As used herein, the term "reaction constraint," or "flux constraint" is intended to mean an upper or lower bound (or boundary) for a reaction's flux. A bound can specify a minimum or maximum flow of mass, electrons or energy through a reaction. A bound can further specify directionality of a reaction. A bound can be a constant value such as zero, infinity, or a numerical value such as an integer and non-integer. Alternatively, a bound can be a variable bound value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "allosteric regulation" refers to the regulation of a protein or enzyme by a molecule that binds to a site other than the primary active site, thereby altering the activity of the enzyme and the corresponding reaction that it regulates.

As used herein, the term "activate" or activation refers to an effect a compound has on another compound, serving to alter the constraints in a positive manner, such as increasing the activity of a reaction. This includes but is not limited to allosteric and non-allosteric regulation of enzymes.

As used herein, the term "inhibit" or inhibition refers to an effect a compound has on another compound, serving to alter the constraints in a negative manner, such as decreasing the activity of a reaction. This includes but is not limited to allosteric and non-allosteric regulation of enzymes.

As used herein, "biomass" refers to a collection of metabolites identified as biomass components, as is common in the art.

As used herein, the term "growth" or "biomass flux" refers to the production of a weighted sum of metabolites identified as biomass components.

As used herein, the term "energy production" refers to the production of metabolites that store energy in their chemical bonds, particularly high energy phosphate bonds such as ATP and GTP.

As used herein, the term "redox equivalent" refers to a metabolite that can alter the oxidation state of other metabolites, generally through the transfer of electrons and or protons.

As used herein, the term "bioactive small molecule" refers to a metabolite that can inhibit or activate another biological compound, including metabolites, proteins, and nucleic acid polymers.

As used herein, the term "cofactor" refers to a metabolite or chemical compound that is required for a catalytic activity of an enzyme to be carried out.

As used herein, the term "optimization problem" refers to a problem whose solution is obtained through the calculation of a minimum (or maximum) value of the objective function.

As used herein, the term "objective function" refers to a physiological or metabolic function that can be described in terms of the data structure of a network, generally in terms of one or more weighted sum or product of reaction fluxes.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space; vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of biological reactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus, a reaction that simply transports a metabolite from the extracellular environment to the cytosol, without changing its chemical composition is solely classified as a translocation, while a reaction such as the phosphotransferase system (PTS) which takes extracellular glucose and converts it into cytosolic glucose-6-phosphate is a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on a cell. While they may be chemically balanced in certain cases, they are typically not balanced and can often have only a single substrate or product. As a matter of convention the exchange reactions are further classified into demand exchange and input/output exchange reactions.

Input/output exchange reactions are used to allow extracellular reactants to enter or exit the reaction network represented by a model. For each of the extracellular metabolites a corresponding input/output exchange reaction can be created. These reactions can either be irreversible or reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reaction can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Depending upon the particular environmental conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in a particular cell or that are desired to simulate the activity of the full set of reactions occurring in the particular cell.

A reaction network data structure or index of reactions used in the data structure such as that available in a metabolic reaction database, as described herein, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction or Gene Ontology (GO) number of the particular metabolic reaction, a subset of reactions to which the reaction belongs, citations to references from which information was obtained, or a level of confidence with which a reaction is believed to occur in a particular cell. A computer readable medium of the invention can include a gene database containing annotated reactions. Such information can be obtained during the course of building a metabolic reaction database or model of the invention as described below.

Flux constraints can be placed on the value of any of the fluxes in a metabolic network. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism.

The methods described herein can be implemented on any conventional host computer system, such as those based on Intel® or AMD® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN or COBOL and compiled using any well-known compatible compiler. The software of the invention normally runs from instructions stored in a memory on a host computer system. A memory or computer readable medium can be a hard disk, floppy disc, compact disc, DVD, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

Data matrices can be represented in a markup language format including, for example, Systems Biology Markup Language (SBML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, Learning XML O'Reilly and Associates, Sebastopol, Calif. (2001).

A computer system of the invention can include a user interface capable of receiving a representation of one or more reactions. A user interface of the invention can also be capable of sending at least one command for modifying the data structure, the flux constraints or the commands for applying the constraints to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to human physiology. Also, the user interface can display a graphical representation of a reaction network or the results of a simulation using a model of the invention.

As used herein, the term "physiological function" is intended to mean an activity of a cell as a whole. An activity included in the term can be the magnitude or rate of a change from an initial state of a cell to a final state of the cell. An activity can be measured qualitatively or quantitatively. An activity included in the term can be, for example, growth, energy production, redox equivalent production, biomass production, compound production, development, flux through a particular reaction or set of reactions, enzyme activity, or consumption of carbon, nitrogen, sulfur, phosphate, hydrogen or oxygen. An activity can also be an output of a particular reaction that is determined or predicted in the context of substantially all of the reactions that affect the particular reaction in a cell or substantially all of the reactions that occur in a cell. Examples of a particular reaction included in the term are production of biomass precursors, production of a protein, production of an amino acid, production of a purine, production of a pyrimidine, production of a lipid, production of a fatty acid, production of a cofactor, production of a bioactive small molecule, flux through a particular reaction or set of reactions, enzyme activity, or transport of a metabolite. The activities or reactions in the physiological function can be increased or decreased. A physiological function can include an emergent property which emerges from the whole but not from the sum of parts where the parts are observed in isolation.

As used herein, the term "metabolic engineering algorithm" refers to a computational method that identifies how metabolic or regulatory processes should be changed to improve chemical production or chemical consumption. Exemplary metabolic engineering algorithms include, without restriction, OptKnock, OptGene, OptORF, OptStrain, SimOptStrain, OptReg, OptForce, CosMos, and FSEOF [3, 5, 6, 7, 8, 9, 10, 11, 12, 13].

As used herein, the term "bi-level optimization" refers to a type of optimization that involves two levels (referred to as outer and inner) of optimization problems, where the inner optimization problem(s) is nested within an outer optimization problem.

As used herein, the term "metabolic function" refers to flux through a particular reaction or set of reactions, and thereby refers to a type of physiological function.

A physiological function of cellular reactions can be determined using a reaction map to display a flux distribution. A reaction map (network map) can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

Methods disclosed herein can be used to determine the activity of a plurality of cellular reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite and metabolism of an alternative carbon source.

Methods disclosed herein can be used to determine genetic variations of a cell or organism that enable it to perform a particular physiological function. The physiological function may comprise, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite, metabolism of an alternative carbon source, or biosynthesis of any desired compound the cell is capable of making. The genetic variations can be determined using the methods described above, wherein the reaction network data structure lacks one or more gene-associated reactions. Alternatively, methods can be used to determine genetic variations when a reaction that does not naturally occur in the cell is added to the reaction network data structure. Deletion of a gene can also be represented in a model of the invention by constraining the flux through the associated reaction(s) to zero, thereby allowing the reaction to remain within the data structure. Thus, simulations can be made to predict the effects of adding or removing genes to or from the cell. The methods can be particularly useful for determining the effects of adding or deleting a gene that encodes for a gene product that performs a reaction(s) in a peripheral metabolic pathway. In one contemplated embodiment, vectors are used for in vivo transfer of genes determined in silico to be required for a desired functioning of the metabolic pathway. Other methods are discussed below or known in the art.

The methods of the invention can be used to determine the effects of one or more environmental components or conditions on an activity of a cell. As set forth above, an exchange reaction can be added to a reaction network data structure corresponding to uptake of an environmental component, release of a component to the environment, or other environmental demand. The effect of the environmental component or condition can be further investigated by running simulations with adjusted values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a cell can be taken up and metabolized. The environmental component can also be a combination of components present for example in a minimal medium composition. Thus, methods disclosed herein can be used to determine an optimal or minimal medium composition that is capable of supporting a particular activity of a cell.

The invention provides methods of generating cells capable of performing a physiological function. Possible genotypes of cells capable of performing a physiological function can first be determined. Cells having the predicted genotypes can then be generated. The cells can be generated by functionally deleting genes or gene products, or increasing or decreasing expression or activity of genes or gene products. In some instances, the cells undergo adaptive evolution to achieve the desired physiological function. Adaptive evolution involves culturing a population of cells for many generations under conditions for which they are not optimally adapted to select for variants with the desired physiological function.

"Functional deletion" or its grammatical equivalents refers to any modification to a cell that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. "Gene" as used herein refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others. In some versions of the invention, "functionally deleted gene product or homolog thereof" means that the gene is mutated to an extent that a gene product or homolog thereof is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., Molecular Cloning: A Laboratory Manual, 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding cell. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding cell.

As used herein, "corresponding cell" refers to a second cell having the same or substantially same genetic and proteomic composition as a first cell, with the exception of genetic and proteomic differences resulting from the modifications described herein for the first cell.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to coding sequences, genes, or gene products described herein (see below) or those identified by the methods described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

The cells of the invention may be modified to express or increase expression of one or more genes involved in carrying out the physiological function. Modifying a cell to express or increase expression of a gene can be performed using any methods currently known in the art or discovered in the future. Examples include genetically modifying the cell and culturing the cell in the presence of factors that increase expression of the gene. Suitable methods for genetic modification include but are not limited to placing the coding sequence under the control of a more active promoter, increasing the copy number of the gene, and/or introducing a translational enhancer on the gene (see, e.g., Olins et al. *Journal of Biological Chemistry*, 1989, 264(29): 16973-16976). Increasing the copy number of the gene can be performed by introducing additional copies of the gene to the cell, i.e., by incorporating one or more exogenous copies of the native gene or a heterologous homolog thereof into the cellular genome, by introducing such copies to the cell on a plasmid or other vector, or by other means. "Exogenous" used in reference to a genetic element means the genetic element is introduced to a cell by genetic modification. "Heterologous" used in reference to a genetic element means that the genetic element is derived from a different species. A promoter that controls a particular coding sequence is herein described as being "operationally connected" to the coding sequence.

The cells of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell is one that contains a recombinant nucleic acid molecule or polypeptide. "Overexpress" as used herein means that a particular gene product is produced at a higher level in one cell, such as a recombinant cell, than in a corresponding cell. For example, a cell that includes a recombinant nucleic acid configured to overexpress an enzyme produces the enzyme at a greater amount than a cell that does not include the recombinant nucleic acid.

The cells of the invention may comprise any type of cell. The cells may be isolated, dispersed, or in the form of an organ or tissue. Exemplary cells comprise microorganisms. The microorganisms may be prokaryotic or eukaryotic. Suitable prokaryotes include bacteria and archaea. Suitable types of bacteria include gram-positive bacteria, gram-negative bacteria, ungrouped bacteria, phototrophs, lithotrophs, and organotrophs. Suitable eukaryotes include yeast and other fungi.

The invention also provides methods for increasing or decreasing compound production or increasing or decreasing select enzyme activities with the cells of the present invention. The methods involve culturing the microorganism in conditions suitable for growth of the cell. In some instances, the cells undergo adaptive evolution to achieve the desired physiological function. The cell either directly produces the desired compound or produces precursors from which the desired compound is spontaneously converted. The desired compound may be any metabolite the cell naturally generates or any metabolite the cell does not naturally generate but is capable of generating through genetic modification. The select enzyme activity may be the activity of an enzyme naturally encoded in the organism's genome or may be an enzyme that is heterologously expressed. Conditions for culturing cells are well-known in the art. Such conditions include providing suitable carbon sources for the particular cell along with suitable micronutrients. For eukaryotic cells and heterotrophic bacteria, suitable carbon sources include various carbohydrates. Such carbohydrates may include biomass or other suitable carbon sources known in the art. For phototrophic bacteria, suitable carbon sources include $CO_2$, which is provided together with light energy.

Methods of producing a desired compound with the cells of the present invention may also include isolating the desired compound from the cell. Methods of isolating various compounds from cells are well-known in the art.

As described in further detail below, the invention further provides microorganisms configured for producing ethanol. The microorganisms comprise a modification that functionally deletes gene products of a set of genes. In preferred versions, the sets of genes are selected from: atpA, atpB, atpC, aptD, atpE, atpF, atpG, and atpH or homologs thereof; a gene selected from tesB, mgsA, glcA, lldP, tpiA, and a gene selected from atpA, atpB, atpC, aptD, atpE, atpF, atpG, and atpH or homologs thereof; tesB, mgsA, dld, ldhA, tpiA, and a gene selected from atpA, atpB, atpC, aptD, atpE, atpF, atpG, and atpH or homologs thereof; glcA, lldP, pgi, and a gene selected from atpA, atpB, atpC, aptD, atpE, atpF, atpG, and atpH or homologs thereof; dld, ldhA, pgi, and a gene selected from atpA, atpB, atpC, aptD, atpE, atpF, atpG, and atpH or homologs thereof; gdhA, glcA, lldp, and a gene selected from atpA, atpB, atpC, aptD, atpE, atpF, atpG, and atpH or homologs thereof; gdhA, dld, ldhA, and a gene selected from atpA, atpB, atpC, aptD, atpE, atpF, atpG, and atpH or homologs thereof; glcA, lldP, and a gene selected from atpA, atpB, atpC, aptD, atpE, atpF, atpG, and atpH or homologs thereof; dld, ldhA, and a gene selected from atpA, atpB, atpC, aptD, atpE, atpF, atpG, and atpH or homologs thereof; ldhA, edd, dld, pgi, and a gene selected from atpA, atpB, atpC, aptD, atpE, atpF, atpG, and atpH or homologs thereof; focA, focB, glcA, and lldp or homologs thereof; focA, focB, dld, and ldhA or homologs thereof; focA, focB, glcA, lldP, and ppc or homologs thereof; focA, focB, dld, ldhA, and ppc or homologs thereof; glcA, lldP, a gene selected from ptsH, ptsI, ptsG, and crr, and a gene selected from atpA, atpB, atpC, aptD, atpE, atpF, atpG, and atpH or homologs thereof; dld, ldhA, a gene selected from ptsH, ptsI, ptsG, and crr, and a gene selected from atpA, atpB, atpC, aptD, atpE, atpF, atpG, and atpH or homologs thereof; ydbK, gdhA, tpiA, and ppc or homologs thereof; tpiA, fpr, and ppc or homologs thereof; glcA, lldP, ppc, and a gene selected from atpA, atpB, atpC, aptD, atpE, atpF, atpG, and atpH or homologs thereof; dld, ldhA, ppc, and a gene selected from atpA, atpB, atpC, aptD, atpE, atpF, atpG, and atpH or homologs thereof; and mgsA, gadA, gdhA, edd, gnd, glcB, aceB, tpiA, and a gene selected from sucA and sucB. A preferred microorganism in which the above-mentioned sets of genes may be isolated is *E. coli*. Homologs of the above-mentioned sets of genes in other microorganisms can be determined by the methods described above.

Some of the above-mentioned genes encode subunits of multi-subunit enzymes. The non-specified subunits of such multi-subunit enzymes may be functionally deleted in addition to or as an alternative to functionally deleting the gene products mentioned above.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

The following examples are intended to illustrate but not limit the invention.

EXAMPLES

In the following examples, we detail the application, function and relevant parameters for each of FaceCon module. We then introduce the concept of shadow constraint (ShadowCon) modules, which can be used to control the degree of coupling once coupling between two fluxes occurs. To illustrate each module's functionality and potential use, we have included the FaceCon and ShadowCon modules as additional inner problems within the OptORF algorithm, to find metabolic gene deletions that couple growth and chemical production and that satisfy additional module criteria. Additionally, to demonstrate the methods are applicable on genome-scale networks we have applied them to identify mutants for ethanol production using the *Escherichia coli* model, iJO1366 [35]. We demonstrate that when there are multiple solutions to metabolic engineering algorithms, the addition of FaceCon and ShadowCon modules allows only those mutants that meet additional criteria to be identified. Aspects of the following examples are described in Tervo et al. [38], which is incorporated herein by reference.

Methods

Most algorithms developed for metabolic engineering focus on maximizing chemical production assuming maximum cellular growth. FaceCon and ShadowCon modules can be integrated into existing mixed integer linear adaptive evolution metabolic engineering algorithms (e.g., OptKnock, OptORF, and their tilted variants, as well as RobustKnock) to allow for greater control over strain designs (FIG. 1) and to filter out designs with undesirable suboptimal behaviors. The resulting bi-level optimization problem is converted into a mixed integer linear programming problem (MILP) using duality theory. It is important to note that the modules and the metabolic engineering algorithm are completely independent subproblems (FIG. 2), which only share the same feasible space (altered by deletions in the outer problem) and integer variables. All continuous variables (e.g., fluxes) are unique to each subproblem. Interestingly, many of these bi-level algorithms include a maximum growth subproblem that determines chemical production capabilities at the maximum growth rate. This subproblem itself can be considered a module of the outer problem that selects gene deletions or reaction knockouts that constrain the maximum growth subproblem. Consequently, the FaceCon and ShadowCon modules could be run in isolation of the maximum growth subproblem if chemical production is not of concern. Additionally, because these modules and the metabolic engineering algorithm share integer variables the combinatorial complexity of the problem does not substantially increase with addition of FaceCon or ShadowCon modules. Instead only additional linear constraints are added which should result in polynomial time scaling as the problem size increases.

Figure 3:
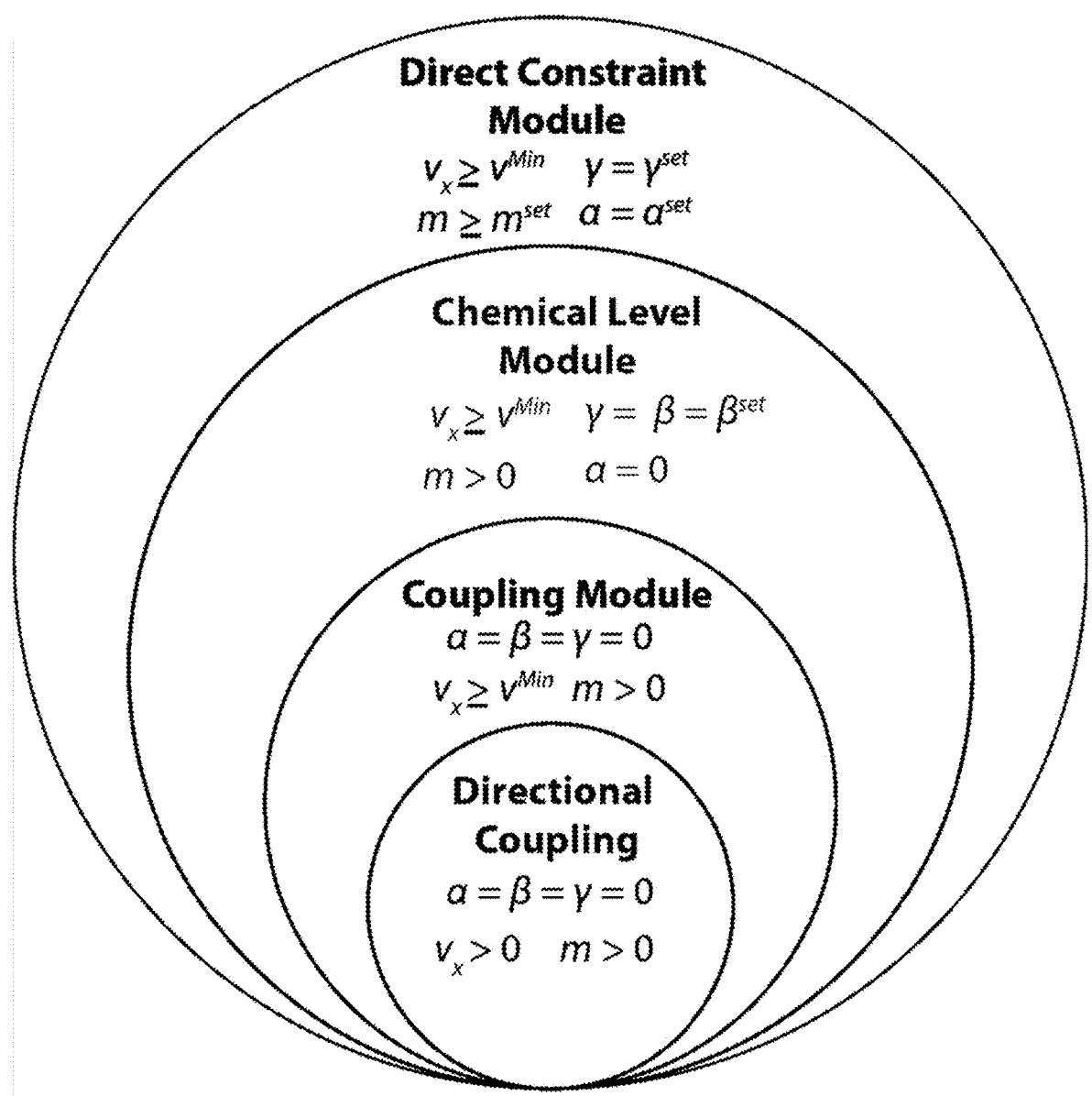
FIG. 3. Hierarchy of FaceCon modules.

The modules described in the present examples include a direct constraint FaceCon module, a chemical level FaceCon module, a coupling FaceCon module, a directional coupling FaceCon module, and a ShadowCon module. The coupling and chemical level modules can be implemented using the same equations as the direct constraint module but with different parameter values (FIG. 3). While all FaceCon modules are written as minimization problems, they can easily be modified to maximization problems (e.g., if one wishes to prevent by-product formation). Additionally, while all modules are included with acceptance criteria written as constraints—thus, not meeting the acceptance criteria forces the problem to be infeasible—such constraints can be reformulated as penalties within the outer metabolic engineering objective, which can be especially useful if finding a feasible solution is particularly challenging.

Metabolic Engineering Algorithm

All modules were incorporated into a gene-deletion focused OptORF [5] (i.e., no regulatory information was considered) and the resulting MILP was written in the General Algebraic Modeling System (GAMS) and solved using CPLEX. A gene deletion penalty of one was used in the OptORF objective and a maximum of twenty gene deletions was used. The standard untilted inner objective function (maximize growth) was used, unless noted otherwise. In cases where a tilted objective function was used in OptORF, the inner objective function was maximize growth rate minus 0.001 times the chemical production rate. Each problem was run for ten thousand seconds (except for the ShadowCon problems which were allowed to run for up to twenty thousand seconds) or until a global optimum was found, whichever occurred first. For the small illustrative network global solutions were found immediately. Using the iJO1366 model, the solver used all the time allotted when the objective for OptORF was tilted (with and without) FaceCon or ShadowCon modules. Similarly, the untilted OptORF required all the time permitted when FaceCon or ShadowCon modules were included. For untilted OptORF without additional modules (stand-alone OptORF), the first six solutions found were each found in ~20-25 minutes; however the next four solutions all took the time allotted. To improve computational performance, all subunits except one were retained (i.e., they cannot be deleted) and all isozymes but one were removed by fixing the relevant binary variables to one and zero, respectively prior to solving (as described previously [36]).

FaceCon Modules

The direct constraint module is the most comprehensive of the FaceCon modules, since with proper parameter selection it can be used to formulate the coupling and direct chemical modules. In the direct constraint module the ratio of $(v_y-\gamma)/(v_x-\alpha)$ is minimized (or maximized). As a result, to ensure the objective remains positive, all fluxes, $v_j$, are broken into their forward and reverse components (Equation 1) and normalized by the variable t (Equations 2 and 3). The resulting variables, $v_{j,direction}'$ and t, are all non-negative.

$$v_j = v_{j,forward} - v_{j,reverse} \quad (1)$$

$$t = \frac{1}{v_{x,direction} - \alpha} \quad (2)$$

$$v_{j,direction}' = \frac{v_{j,direction}}{v_{x,direction} - \alpha} = v_{j,direction} \cdot t \quad (3)$$

Using these transformations, the direct constraint module has the following form:

$$\min(\text{or max})m = \frac{v_{y,direction} - \gamma}{v_{x,direction} - \alpha} = v_{y,direction}' - \gamma \cdot t \quad (4)$$

$$\sum_{j \in R} S_{ij}(v_{j,forward}' - v_{j,reverse}') = 0, \forall i \in M \quad (5)$$

$$v_{x,direction}' = 1 + \alpha \cdot t \quad (6)$$

$$v_{x,direction}' \geq v_x^{min} \cdot t \quad (7)$$

Transformed Domain Constraints (8)

$$v_{j,forward}' \leq v_j^{UpperLimit} \cdot t, \forall j \in R \quad (9)$$

$$v_{j,forward}' \leq -v_j^{LowerLimit} \cdot t, \forall j \in R \quad (10)$$

$$v_{j,forward}' \leq 0, \forall j \in R: a_j = 0 \quad (11)$$

$$v_{j,reverse}' \leq 0, \forall j \in R: a_j = 0 \quad (12)$$

$$v_x^{min} \geq \alpha \quad (13)$$

Where $\alpha$ and $\gamma$ are parameters corresponding to the coordinates on a $v_x$–$v_y$ plane through which a line with the smallest (or largest) calculable slope (m) is found that also goes through the feasible space within a user-defined region (Equation 7). Equation 5 enforces the steady-state mass balances in the transformed flux space. Here $S_{ij}$ is the stoichiometric matrix where i and j refer to metabolites and reactions, respectively. M and R are the set of all reactants and reactions within a model. Equation 6 is a linear rearrangement of Equations 2 and 3. Equation 7 allows the user to define the region where the feasible space constraints will be enforced (e.g., where $v_x$ is greater than $v^{min}$). Thus, for the module to be feasible there must be at least one non-trivial flux distribution within the user-defined region. Additional optional transformed constraints (Equation 8) can be included that specify the user-defined region (or domain) over which the feasible space constraints apply (e.g., $v_{x,direction}' \leq v_x^{Max} \cdot t$, such a constraint can be useful to define multiple excluded regions with varying slopes, m). Equations 9-12 limit the flux of any reaction to its bound or to zero if the reaction has been deleted by the metabolic engineering algorithm (indicated by the binary variable $a_j$ being zero). In order to prevent the module from being infeasible or unbounded, t must be finite and positive and so $v_x$ must be greater than $\alpha$ (Equation 13).

The direct constraint module is included in the metabolic engineering algorithm as an inner problem (FIG. 1). The variables in the direct constraint module are independent of the variables in other inner problems (i.e., the optimal flux distributions for the different inner problems are not necessarily the same). To ensure the module satisfies additional design criteria, the minimum slope, m, needs to be greater (or less than in the case of maximization) than, $m^{set}$, defined by the user. This criterion is enforced by either including a constraint (Equation 14) in the outer problem of the metabolic engineering algorithm or by modifying the outer objective to favor mutants that satisfy this acceptance criterion. To convert the resulting bi-level problem to a single level MILP, the inner optimization problem(s) can be replaced by the set of their primal and dual constraints and equating the primal and dual objectives.

$$m \geq m^{set}, \text{ if min problem}$$

$$m \leq m^{set}, \text{ if max problem} \quad (14)$$

Shadow Con Module

In addition to feasible space constraints on the allowed feasible region, constraints can also be applied to the initial slope where coupling begins along the $v_x$ axis using the following formulation:

$$\max v_x \quad (15)$$

$$\sum_{j \in R} S_{ij} \cdot v_j = 0, \forall i \in M \quad (16)$$

$$v_j \leq v_j^{UpperLimit} \cdot a_j, \forall j \in R \quad (17)$$

$$v_j \geq v_j^{LowerLimit} \cdot a_j, \forall j \in R \quad (18)$$

Domain Constraints (19)

$$v_y = \varepsilon \quad (20)$$

Here, $v_x$ is maximized while satisfying steady-state mass balances (Equation 16), flux lower and upper limits (Equation 17 and 18), and an additional constraint fixing $v_y$ (Equation 20) such that the optimal solution to Equations 15-20 is positioned near the point where the degree of coupling between $v_y$ and $v_x$ (i.e., how a change in $v_y$ will affect the maximum value of $v_x$) should be calculated.

While developed independently, the above optimization problem is similar to that used in FastPros [14]. However, in contrast to FastPros the ShadowCon module is included directly as an inner subproblem in the metabolic engineering algorithm (FIG. 1). Using this inner subproblem, the degree (or slope) of coupling for an OptORF proposed mutant can be controlled. Moreover, because ShadowCon uses a mixed integer formulation instead of a greedy algorithm, our approach will not get stuck in local maxima or minima if strains with a large or small shadow price are desired.

The bi-level problem, created by including a ShadowCon module into a metabolic engineering algorithm (like OptORF or OptKnock), is converted to a single level MILP, by replacing the inner optimization problem(s) with their set of primal and dual constraints and equating the primal and dual objectives. The dual variable (or shadow price) corresponding to Equation 20 is the partial derivative representing how the maximum value for $v_x$ would change if the value for $\varepsilon$ (or $v_y$) changed. Using this relation, we can relate the slope (m) for the line of coupling between $v_y$ and $v_x$ as follows:

$$m = \frac{\partial v_y}{\partial v_x} = \left(\frac{\partial v_x}{\partial \varepsilon} \cdot \frac{\partial \varepsilon}{\partial v_y}\right)^{-1} = \frac{1}{u^{shadow}} \quad (21)$$

Thus, $u^{shadow}$ can be used as a proxy for the potential change in the $v_y$ with respect to a change in $v_x$. In order to ensure that the optimal value for $u^{shadow}$ is unique (i.e., $u^{shadow}$ takes the value of the inverse slope of the line of interest), it is critical to select a value of ε such that the optimal solution ensures that Equation 20 is binding, which is guaranteed for any feasible solution, and that $v_y$ is a basis variable. To accomplish this, it is sufficient to pick an ε such that the new optimum does not fall upon a preexisting pivot (i.e., if the solution is not degenerate, the dual solution is unique [37]). See supplementary material of [38]. For example, when both ε and $v_y^{LowerLimit}$ are zero, $u^{shadow}$ becomes unbounded from above and thus may underestimate the slope, m. This occurs because Equations 18 and 20 are simultaneously binding for $v_y$. Consequently, their two shadow prices can both be increased in conjunction, counteracting one another such that there is no net increase in the objective. To avoid this problem we set the value for c equal to 0.001.

Once the primal and dual for the ShadowCon module have been included in the metabolic engineering algorithm, acceptance criteria constraints (limiting the value for m) can be included in the outer problem (Equations 22 and 23):

$$m > m^{min} \to u^{shadow} < \frac{1}{m^{min}} \quad (22)$$

$$m < m^{max} \to u^{shadow} > \frac{1}{m^{max}} \quad (23)$$

Where $m^{min}$ and $m^{max}$ are the minimum and maximum allowable slopes, respectively. Additional optional constraints for the ShadowCon module can be added to the outer problem to mimic simple coupling conditions and further filter possible solutions:

$$v_x^{min} \leq v_x \leq v_x^{max} \quad (24)$$

$$v_x^{Opt} - v_x \geq \Delta v_x^{min} \quad (25)$$

Here equation 24, makes use of user-defined parameters, $v_x^{min}$ and $v_x^{max}$, to define a region where coupling between $v_x$ and $v_y$ must occur. Alternatively, equation 25, can be added to require a minimum distance $\Delta v_x^{min}$ between the optimal OptORF solution ($v_x^{Opt}$) and where coupling actually begins.

Equations 22 and 23 allow the allowable initial coupling slope to be constrained directly. If instead a particular initial slope value is desired ($m^{set}$), then the slope can instead be optimized to be close to this value. This is accomplished by adding Equations 26-27 to the outer problem and using a new outer objective function (Equation 28) instead of the OptORF objective function.

$$\Delta m^{inv} \geq m^{penalty}\left(\frac{1}{m^{set}} - u^{shadow}\right) \quad (26)$$

$$\Delta m^{inv} \geq -m^{penalty}\left(\frac{1}{m^{set}} - u^{shadow}\right) \quad (27)$$

$$\max \sum_{j \in R} v_j^{Opt} - \delta \cdot \sum_{g \in Nolsozyme} (1 - KO_g) \cdot GW_g - \Delta m^{inv} \quad (28)$$

Here $v_j^{Opt}$ are the fluxes in the metabolic engineering subproblem (in OptORF, for example, the fluxes corresponding to the maximum growth rate), δ is the gene deletion penalty (which was set to 1 in these examples), and $ko_g$ are binary gene deletion variables where a value of 0 indicates the gene (g) is deleted. Only the $KO_g$ variables that do not have isozymes or that represent a group of isozymes are considered (denoted as the gene subset Nolsozyme) in the objective function (Equation 28), since all isozymes but one were removed by fixing the relevant $KO_g$ to zero (to improve runtime performance). $GW_g$ are weighting parameters indicating how many other genes need to be deleted to abolish activity due to other isozymes. The $\Delta m^{inv}$ is a non-negative variable that represents the absolute penalized difference between $1/m^{set}$ and $u^{shadow}$, where the $m^{penalty}$ parameter is used to weight the difference between $1/m^{set}$ and $u^{shadow}$ (in these examples $m^{penalty}$ was set to 1,000). Additional constraints (Equations 24-25) can also be included to define the region where coupling occurs. The difference between the optimal OptORF solution ($v_x^{Opt}$) and where coupling actually begins ($v_x$) can also be maximized, by including and weighting this difference in the objective function (Equation 28)—not shown. Constraints can also be imposed to restrict the minimum and maximum numbers of gene deletions and to prevent solutions that require deletions of genes that have been shown to be essential experimentally.

Mandatory Feasible Spaces

Mandatory feasible spaces are regions created by inserting any module of the following form:

$$\sum_{j \in R} S_{ij} \cdot v_j = 0, \forall\, i \in M \tag{29}$$

$$v_j \leq v_j^{UpperLimit} \cdot a_j, \forall\, j \in R \tag{30}$$

$$v_j \geq v_j^{LowerLimit} \cdot a_j, \forall\, j \in R \tag{31}$$

Domain Constraints (32)

Where sets R and M are the sets of all reactions and metabolites respectively in the organism, $v_j$ represents the amount of flux through reaction, j, $S_{ij}$ is the stoichiometric matrix for the organism studied, $a_j$ is a binary variable indicating the presence of a reaction where 0 indicates a reaction knockout, and $v_j^{UpperLimit}$ and $v_j^{LowerLimit}$ indicate the upper and lower bound restrictions, respectively, of a given reaction, j. Domain constraints (equation 32) encompass any additional constraints that limit the domain of any given flux, $v_j$ (e.g., $v_j \geq v^{min}$). Based on this formulation, we define a mandatory feasible space to be one such that there exists at least one non-trivial flux distribution, $v_j^*$, that satisfies (equations 29-32). Based on this definition, it is easy to show that any constraint which excludes a non-zero flux value (e.g., $v_j > v_j^{LowerLimit} > 0$) will necessarily result in a mandatory feasible space. This becomes important for any FaceCon module that uses domain type constraints, as it will require that a solution exists within the user-defined region or the entire problem will become infeasible. While this can be potentially problematic, such spaces can also be used to tailor the feasible space of your final solution such that a particular solution must be accessible within a user-defined region (e.g. there must be a solution that satisfies equations 29-32 and where $v_j \geq v^{Min}$). Thus, while we don't treat them as such, mandatory feasible spaces can be considered a fourth type of feasible space constraint and are embedded in other FaceCon modules to enforce various conditions.

Coupling Module

Both the coupling and chemical level modules can be formulated using the direct constraint equations given above. Here we describe simpler formulations of the coupling and chemical level modules.

The coupling module enforces coupling (i.e., flux through $v_y$ implies flux through $v_x$ while the opposite is not strictly true) between two variables after a user specified minimum coupling point, $v_x \geq v_x^{min}$. To accomplish this task, each flux $v_j$ must be separated into two non-negative variables $v_{j,forward}$ and $v_{j,reverse}$ representing the forward and reverse flux through that reaction (equation 33). All fluxes are then subsequently transformed so that minimum ratio of $v_y$ to $v_x$ can be calculated using linear programming techniques. This is accomplished by multiplying the entire linear program (LP) by t' the inverse of the variable which is to be coupled with $v_y$ (equations 34 and 35).

$$v_j = v_{j,forward} - v_{j,reverse} \tag{33}$$

$$t' = \frac{1}{v_{x,direction}} \tag{34}$$

$$\hat{v}_{j,direction} = \frac{v_{j,direction}}{v_{x,direction}} = v_{j,direction} \cdot t' \tag{35}$$

Using the transformed variables, the coupling module takes the following form:

$$\min(\text{or max})m = \frac{v_{y,direction}}{v_{x,direction}} = \hat{v}_{y,direction} \tag{36}$$

$$\sum_{j \in R} S_{ij}(\hat{v}_{j,forward} - \hat{v}_{j,reverse}) = 0, \forall\, i \in M \tag{37}$$

$$\hat{v}_{x,direction} = 1 \tag{38}$$

$$\hat{v}_{x,direction} \geq v_x^{min} \cdot t' \tag{39}$$

$$\hat{v}_{j,forward} \leq v_j^{UpperLimit} \cdot t', \forall\, j \in R \tag{40}$$

$$\hat{v}_{j,reverse} \leq -v_j^{LowerLimit} \cdot t', \forall\, j \in R \tag{41}$$

$$\hat{v}_{j,forward} \leq 0, \forall\, j \in R: a_j = 0 \tag{42}$$

$$\hat{v}_{j,reverse} \leq 0, \forall\, j \in R: a_j = 0 \tag{43}$$

$$t', \hat{v}_{j,direction} \geq 0 \tag{44}$$

Where m is the calculated slope of the line from the origin which goes through the feasible solution space in the user-defined region. Any value greater than 0 indicates coupling. $v_y$ is the flux to which $v_x$ will be coupled. Equation 37 is the transformed form of the mass balance equations where $S_{ij}$ is the stoichiometric matrix entry for metabolite i and reaction j. Sets R and M are the sets of all reactions and reactants, respectively. Equation 35 is the combination of equations 34 and 35 for $v_x$. Equation 39 enforces user-defined domain constraints on $v_x$. Equations 40 and 41 are the transformed upper, $v_j^{UpperLimit}$, and lower bounds, $v_j^{LowerLimit}$, for each reaction, while equations 42 and 43 enforce any reaction deletions that have been selected in the outer problem of the metabolic engineering algorithm. Here $a_j$ is a binary variable indicating whether the reaction is absent ($a_j=0$) or present ($a_j=1$) in the mutant. In addition, all variables must be non-negative (equation 44). Once the module has been added to the metabolic engineering problem, an acceptance criterion must be added to the outer problem to enforce the coupling constraint. For the coupling module, the minimum calculated slope must simply be non-zero (Equation 45).

Acceptance Criterion:

$$m > 0 \tag{45}$$

As shown, the coupling module will find mutants that are either weakly or directionally coupled. If only directional coupling is desired then $v_x^{min}$ should be set to 0, and thus Equation 39 can be omitted. If only weak coupling is desired than an additional sub-problem needs to be added ensuring that no coupling exists for some values of $v_x$ less than $v_x^{min}$ (see below for details).

Chemical Level Module

The chemical level module requires that any mutant proposed by a metabolic engineering algorithm must have more than some minimal flux level, β, for a given reaction, $v_y$, within a user-specified domain (e.g., $v_x \geq v_x^{min}$). This is accomplished by creating a rectangular excluded region such that no feasible solution for the mutant can exist. Such a module can be especially useful for example in ensuring that one achieves a minimal chemical production rate when biomass production is above some threshold. Unlike the other two FaceCon modules, the flux variables do not have to be transformed. The module objective is formulated as follows:

$$\min(\text{or max}) z = v_y - \beta \quad (46)$$

$$\sum_{j \in R} S_{ij} \cdot v_j = 0, \forall\, i \in M \quad (47)$$

$$v_j \leq v_j^{UpperLimit} \cdot a_j, \forall\, j \in R \quad (48)$$

$$v_j \geq v_j^{LowerLimit} \cdot a_j, \forall\, j \in R \quad (49)$$

Domain Constraints(e.g., $v_x \geq v_x^{min}$) $\quad (50)$

All variables and parameters are as defined above. For the present examples, we assume that any domain constraint is one dimensional (e.g., the 1D constraint, $v_x \geq v_x^{min}$). The acceptance criterion used in the outer problem for the direct chemical module simply requires that the objective, z, be a non-negative value if the problem is written as a minimization problem, or non-positive if the problem is written as a maximization problem (such as for avoiding by-product formation). Additionally, for the special case of byproduct minimization where $\beta=0$, multiple reactions can be blocked simultaneously by changing the objective (equation 46) to a summation over all unwanted reactions (as long as their fluxes are all non-negative).

$z \geq 0$, if min problem $z \leq 0$, if max problem $\quad (51)$

Results

Figure 4A:
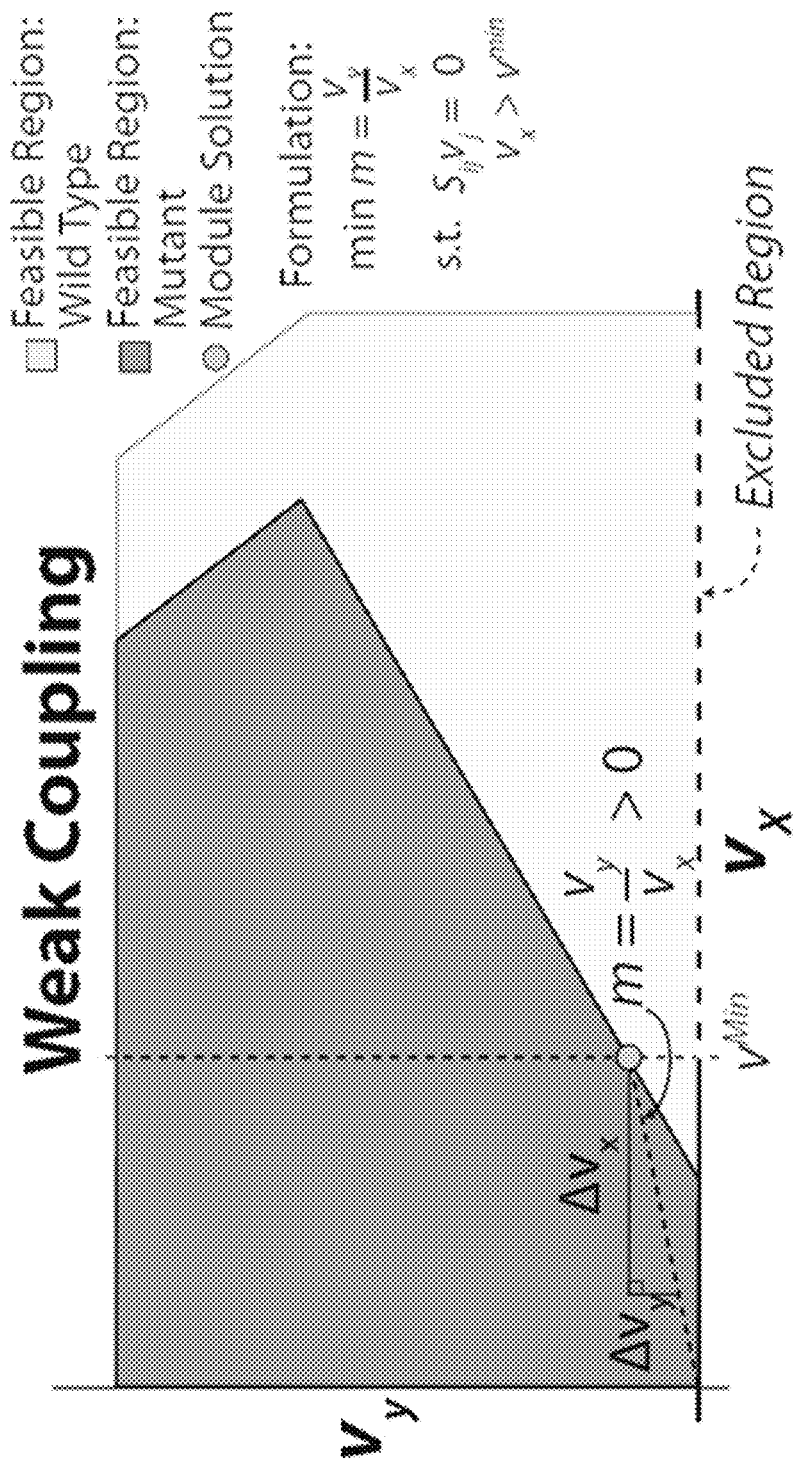
FIGS. 4A-C. Examples of FaceCon modules and their effects on a strain's feasible region.
Figure 4B:
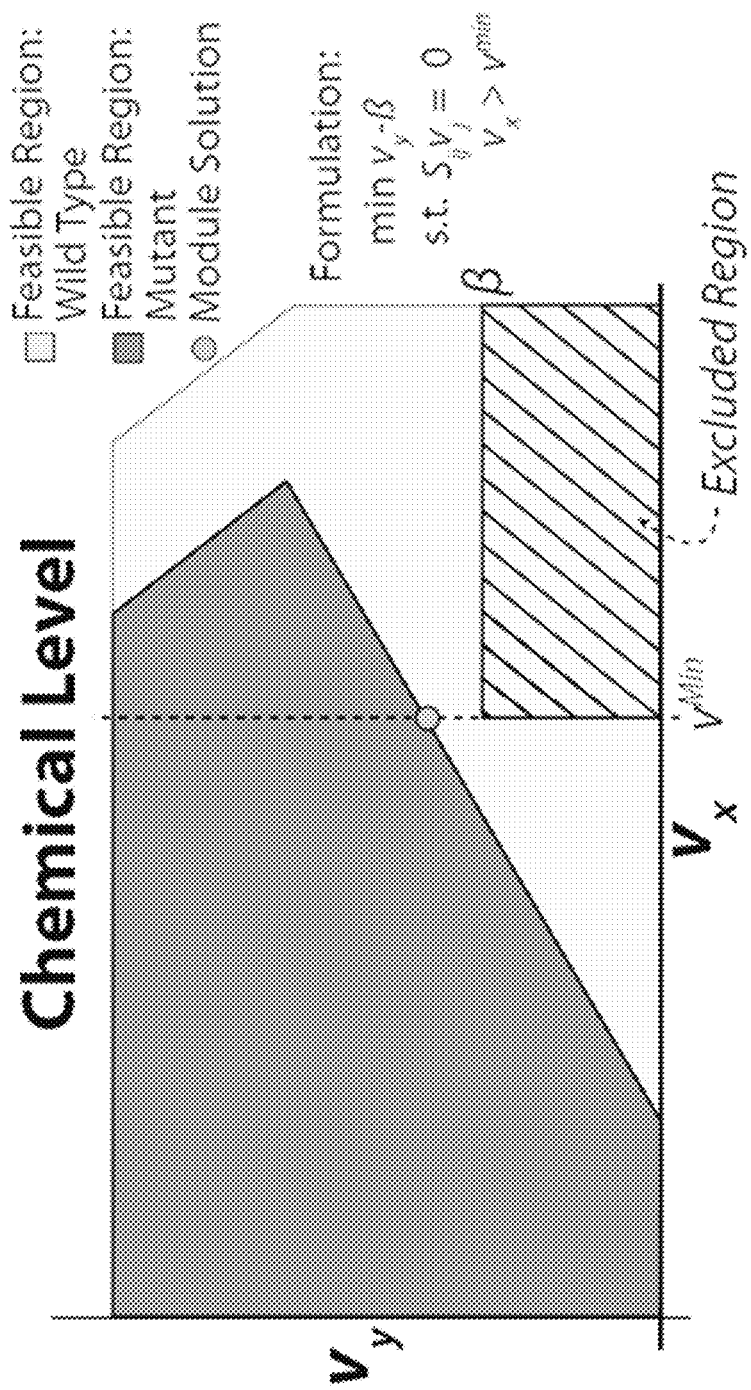
Figure 4C:
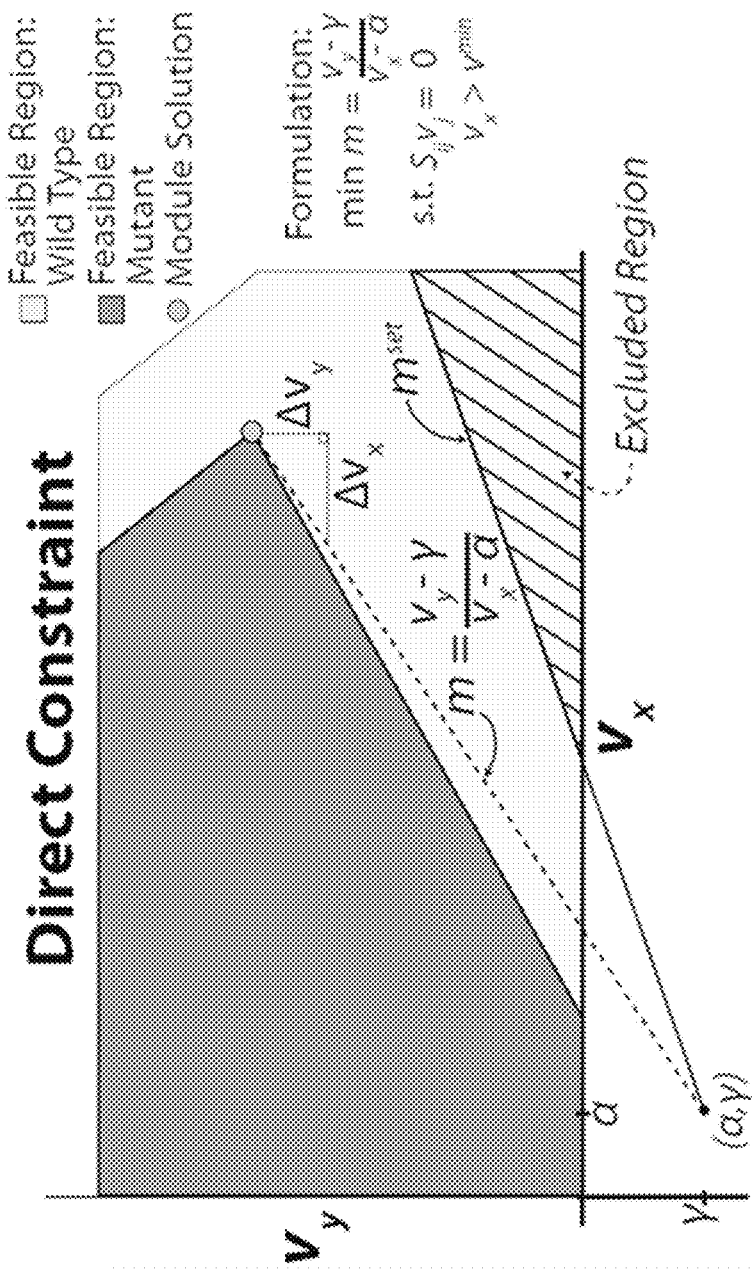

FaceCon and ShadowCon modules are sub-problems, formulated such that their resulting inner objective values can be used to test acceptance criteria of mutants being evaluated by the metabolic engineering algorithm (see FIGS. 4A-4C). While the formulations for each module are distinct they all share certain features. Firstly, all FaceCon modules check that no feasible solution exists within a user-defined region (e.g., region where flux $v_x$ is greater than $v^{min}$). Consequently, FaceCon modules create a mandatory feasible region (i.e., a region within which a non-trivial feasible solution must exist for any mutants proposed by the strain design algorithms). By evaluating these regions, FaceCon modules allow researchers to find mutants that meet additional criteria, which would not be possible using existing metabolic engineering algorithms alone. Below we describe the parameters and unique features of the FaceCon and ShadowCon modules. A summary of all modules included in the present examples and their usage is provided in Table 1.

TABLE 1

Summary of modules and their usage.

| | Module Name | Description | Parameters | Usage |
|---|---|---|---|---|
| FaceCon | Coupling Module | Module allows researcher to enforce weak or directional coupling. To enforce only weak coupling a second sub-problem is added. | $v^{min}$, $\delta^*$, $\sigma^*$ | Can be used to define the nature of coupling proposed by metabolic engineering algorithms. Can be useful when proposals tend to generate sickly mutants. |
| | Chemical Level Module | Module allows researchers to define minimal or maximal chemical production limits, $\beta$, beyond a user defined point $v^{min}$ | $v^{min}$, $\beta$ | Can be used to eliminate undesired by-products or to define minimal chemical production criteria. |
| | Direct Constraint Module | Module allows researchers to create an exclusion region of their own design, defined by the line going through the point ($\alpha$, $\gamma$) with the slope $m^{set}$ | $v^{min}$, $\alpha$, $\gamma$, $m^{set}$ | Can be used to propose co-production or co-utilization of metabolites. All FaceCon modules are special cases of the direct constraint module. |
| Other | ShadowCon Module | Module allows greater control over the degree of coupling once it has initiated | $m^{min}$, $m^{max}$ | Can be used to vary the intensity of selective pressure on a reaction when coupled to growth rate. |

*Parameters are only used when additional module sub-problems are required (e.g., when only weakly coupled mutants are desired).

Coupling Module

The coupling module (FIG. 4A) works to enforce directional or weak coupling between two fluxes ($v_x$ and $v_y$, where a non-zero $v_x$ implies a non-zero $v_y$). By altering the formulation and parameters, the coupling module can be used to identify mutants with directional coupling (i.e., $v_x$ implies $v_y$ for all values of $v_x$—effectively FOCAL sans media selection constraints), weak coupling (i.e., $v_x$ implies $v_y$ if $v_x$ is greater than a positive, user-defined value, $v^{min}$, and $v_x$ does not imply $v_y$ for some non-zero value of $v_x$ less than $v^{min}$), or either directional or weak coupling. Inclusion of such modules results in mutants having an infeasible region containing the $v_x$-axis above $v^{min}$ (for the directional coupling case $v^{min}$ is zero). A coupling module adds a mixed-integer linear program (MILP) sub-problem to the strain design algorithm, and finds the minimum ratio (m) of $v_y/v_x$ within the user-defined region ($v_x > v^{min}$). To meet the acceptance criterion of this module, m must be non-trivial. In addition, to only find mutants with weak coupling (i.e., there also exists some $v_x > 0$ where $v_y$ can be 0 and thus the fluxes are not directionally coupled) another sub-problem is added to ensure that $v_y$ can be zero for some values of $v_x$ less than $v^{min}$. A coupling module determines the line going through the origin with the smallest slope that lives in the feasible space where $v_x > v^{min}$ for a given mutant.

Figure 5A:
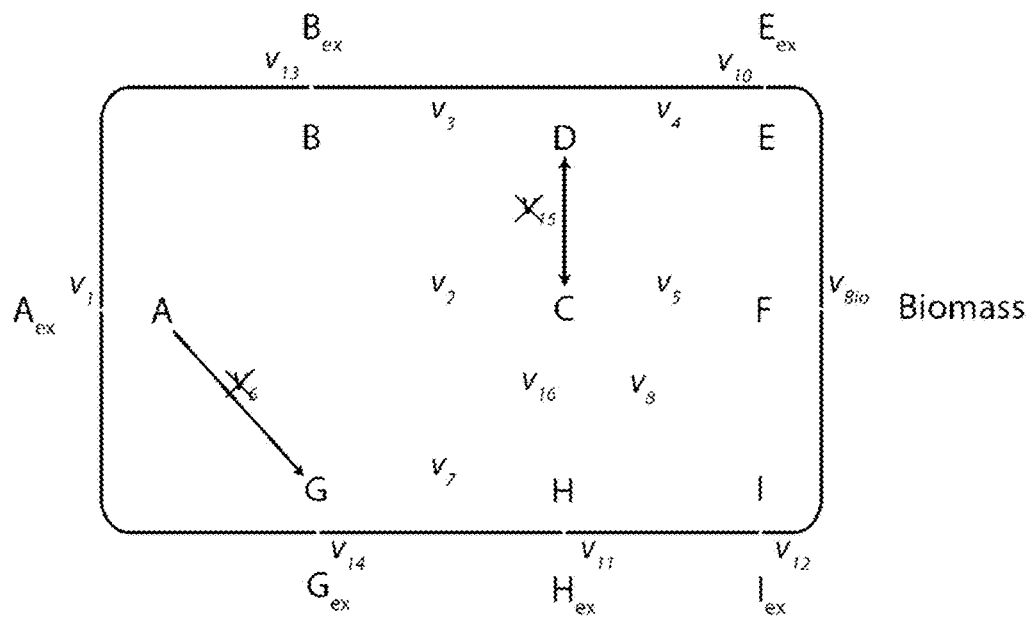
Figure 5B:
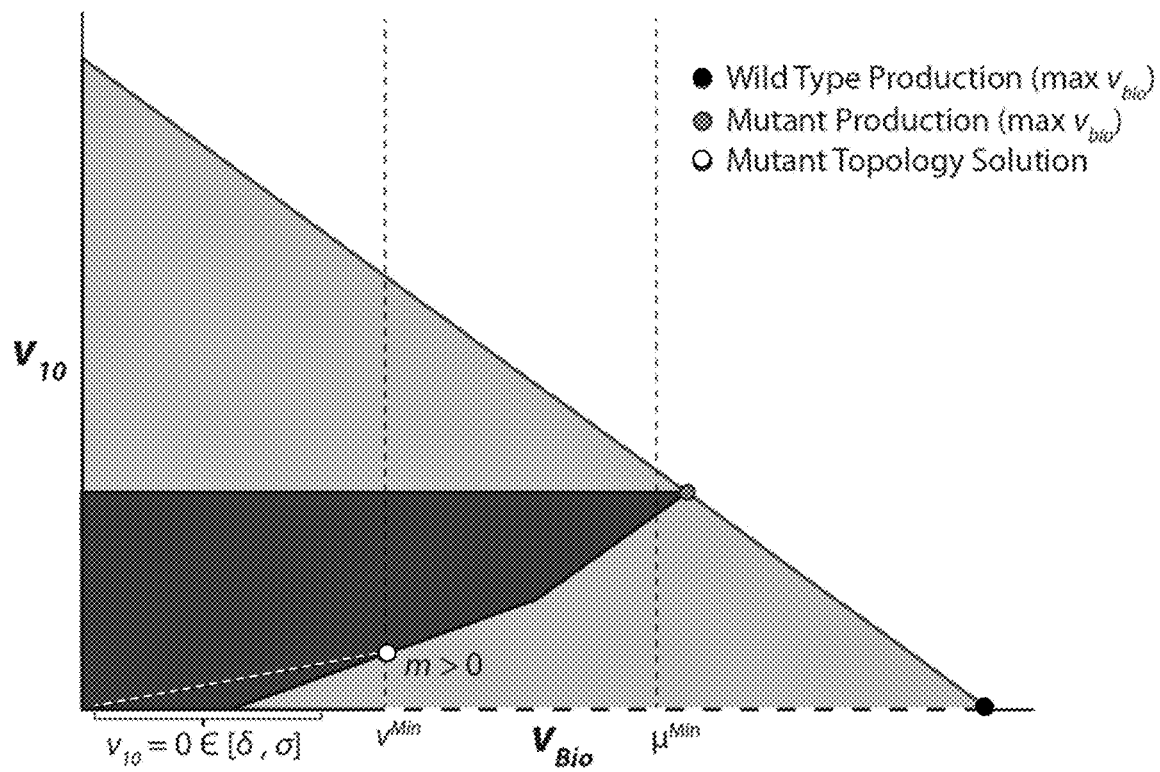

An illustrative example (FIGS. 5A-5B) is provided to demonstrate the functionality of the coupling module to only find mutants with weak coupling (we have previously shown examples of directional coupling involving substrate co-utilization[32]). In this example, OptORF is used to design a strain that maximizes the production of $E_{ex}$ ($v_{10}$) while maintaining a minimum biomass production rate ($v_{bio}>\mu^{min}$). In addition, two sub-problems were added such that a proposed mutant found by OptORF must have a weak coupling phenotype (coupling between $v_{10}$ and $v_{bio}$ occurs only for certain values of $v_{bio}$). An optimization sub-problem is added which minimizes the ratio of $v_{10}/v_{bio}$, when $v_{bio}>v^{min}$. (Note that by setting lower values for $v^{min}$ a stronger selection pressure for chemical production can be achieved since more values of $v_{bio}$ must result in chemical production). Then another sub-problem is added to ensure that directional coupling does not occur for some value of $v_{bio}$ within a defined range (i.e., $v_{10}=0$ for $\delta<v_{bio}<\sigma$, where $\delta$ and $\sigma$ are user-selected values greater than 0 and less than $v^{min}$, respectively. Adding these constraints guarantees that coupling will not occur for values of $v_{bio}\leq\delta$). The inclusion of this second sub-problem guarantees that there is at least one solution where $v_{10}$ is 0 and cellular growth is still possible, thus ensuring the weak coupling criteria is met. Such solutions may be of value when coupling is desired but directional coupling solutions are thought to be too deleterious to the cell's fitness. The solution proposed when these two sub-problems are included in OptORF involves knocking out fluxes $v_6$ and $v_{15}$, which works to couple both $A_{ex}$ and $B_{ex}$ consumption to the production of $E_{ex}$ while allowing $G_{ex}$ to be directed entirely to biomass production. With these fluxes eliminated, simultaneous consumption of $A_{ex}$, $B_{ex}$, and $G_{ex}$ will result in $E_{ex}$ production at the maximum growth rate; however, consumption of $G_{ex}$ alone can still proceed without any $E_{ex}$ production. The feasible region for this mutant growing in the presence of $A_{ex}$, $B_{ex}$, and $G_{ex}$ is shown in FIG. 5B.

Chemical Level Module

Figure 6A:
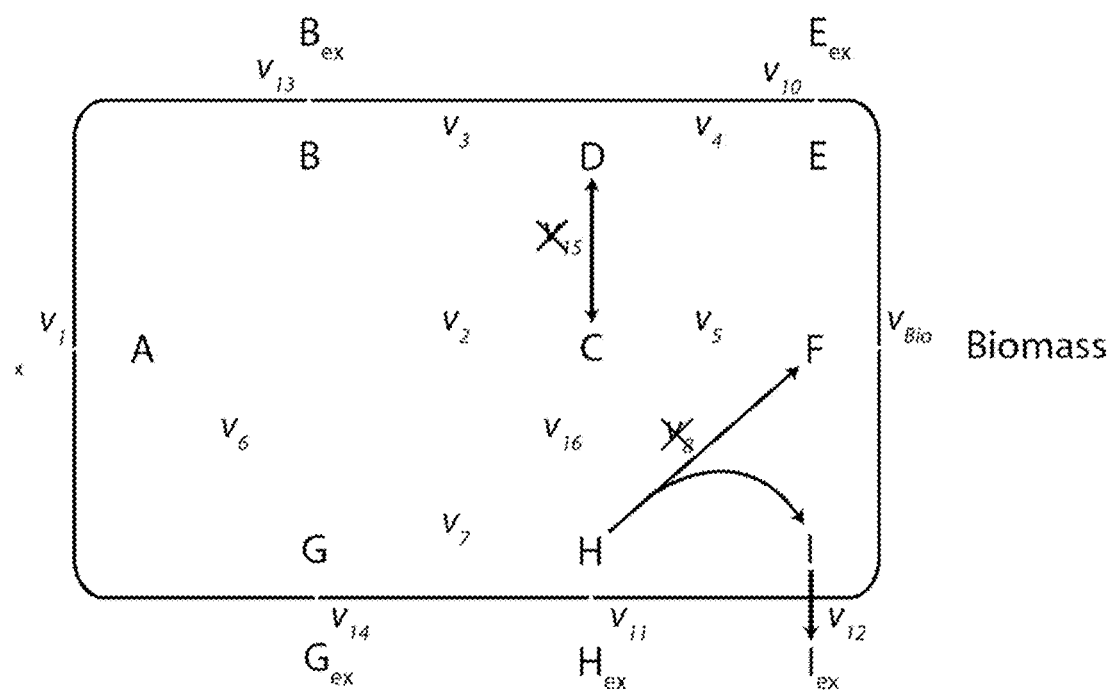
FIGS. 6A-C depict results of a chemical level module added to prevent any production of the undesired compound $I_{ex}$.
Figure 6B:
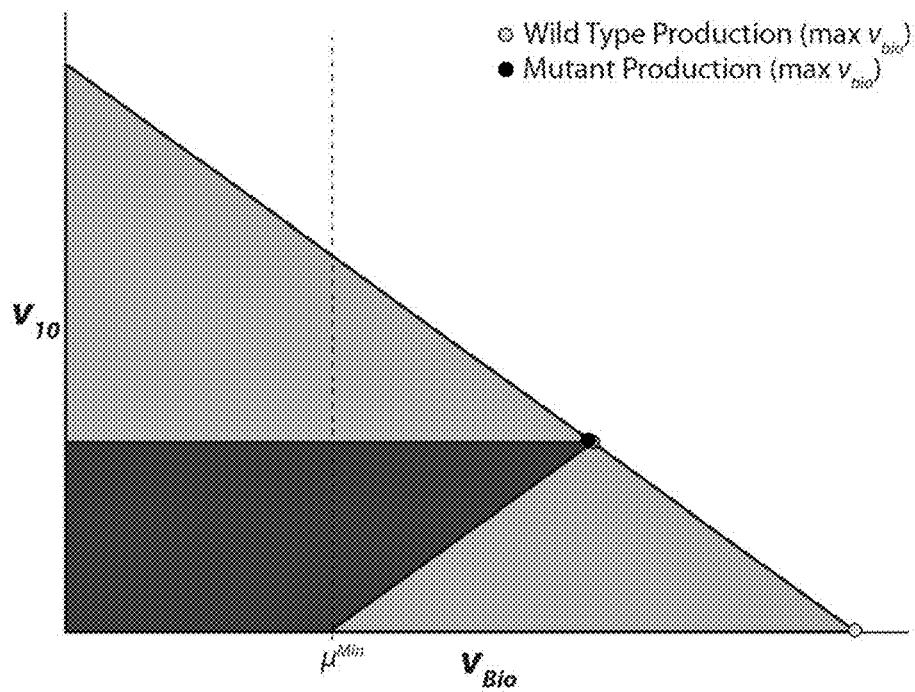
Figure 6C:
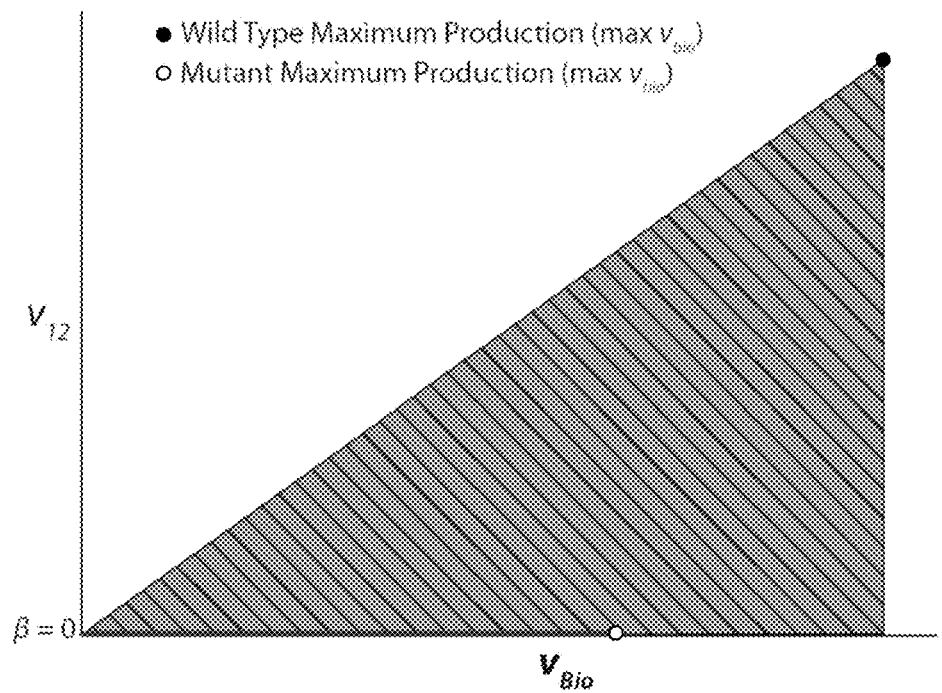

The chemical level module works to find the minimum (or maximum) flux value through a reaction of interest ($v_y$, e.g., chemical production) when flux through another reaction ($v_x$, e.g., growth) exceeds some threshold ($v^{min}$). When this module is embedded in a strain design algorithm the resulting strain proposed must have a value of $v_y$ greater (or less) than a user-defined requirement, $\beta$, when $v_x$ is greater than $v^{min}$ (FIG. 4B). This type of module results in a rectangular excluded region of height, $\beta$. Such a module can, for example, be useful in guaranteeing a minimum amount of production at certain growth rates (and hence a minimum productivity) or limiting the production of undesired by-products. In the illustrative example, the chemical level module was used in conjunction with OptORF to maximize the production of $E_{ex}$ while guaranteeing that no undesired by-product $I_{ex}$ was produced (FIGS. 6A-6C). To ensure a mutant with this phenotype was proposed, the chemical level module was used to calculate the maximal amount of flux through reaction, $v_{12}$. Since no by-product formation was desired, both $v^{min}$ and $\beta$ were set to zero resulting in an excluded region across the entire $v_{bio}$-$v_{12}$ sub-space. With these additional criteria, OptORF proposed knocking out fluxes $v_{15}$ and $v_8$, which prevents production of $I_{ex}$ and also results in weak coupling between $v_{10}$ and $v_{bio}$. The feasible region for the mutant is shown in FIGS. 6B and 6C.

Direct Constraint

The Direct Constraint module (FIG. 4C) is the most multifunctional of the FaceCon modules described. This module creates a line through the point ($\alpha,\gamma$) with slope $m^{set}$; all points below (or above) the line must be excluded from the feasible region of any proposed mutant. The module works by determining the line with the smallest (or largest) slope (m) going through a point within the user-defined region of the feasible $v_x$-$v_y$ sub-space and the point, $(v_x,v_y)=(\alpha,\gamma)$ where $\alpha$ and $\gamma$ are defined by the user. Once this slope has been calculated, a proposal is accepted on the condition that m is greater (or less) than a user-defined slope, $m^{set}$.

Figure 7A:
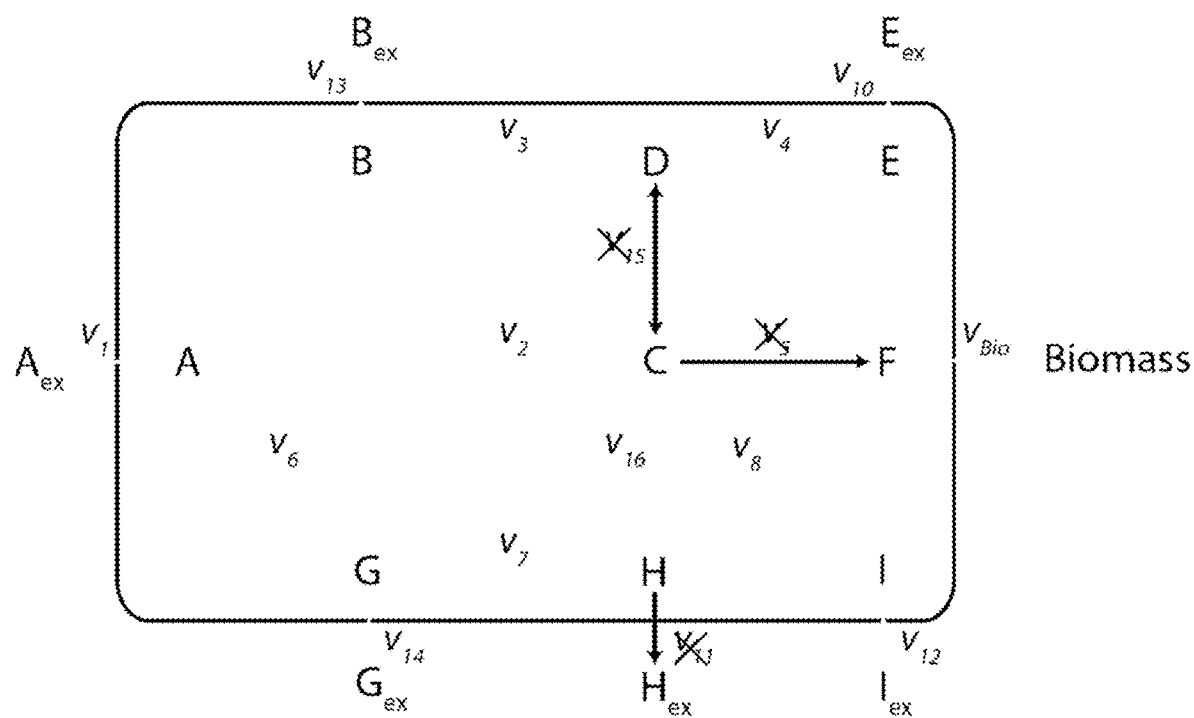
Figure 7B:
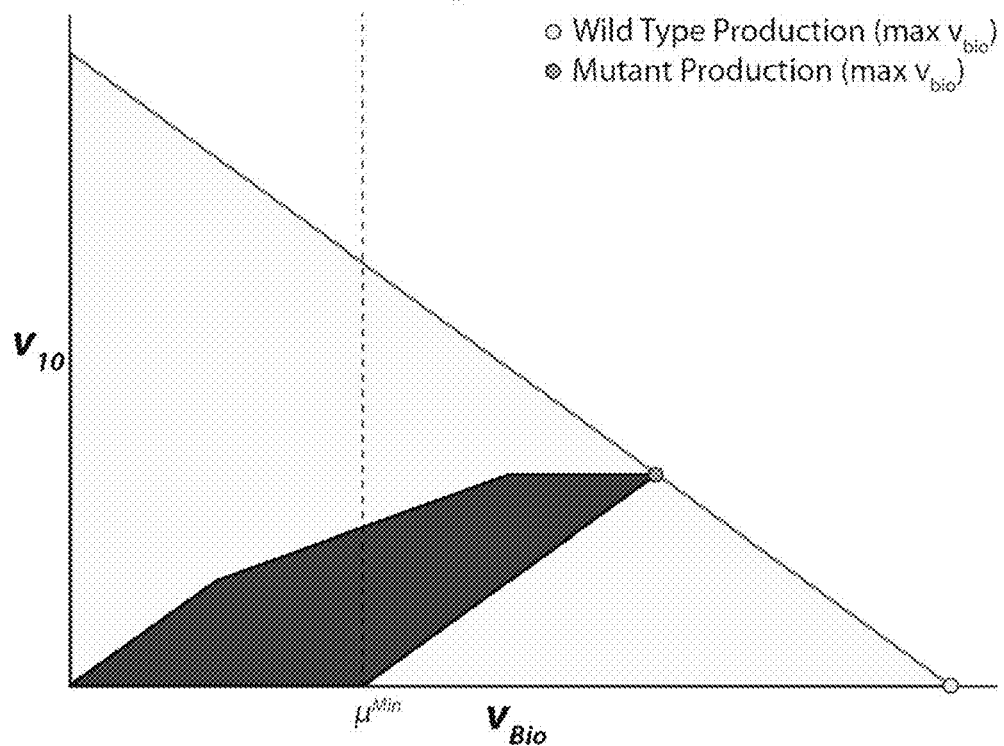
Figure 7C:
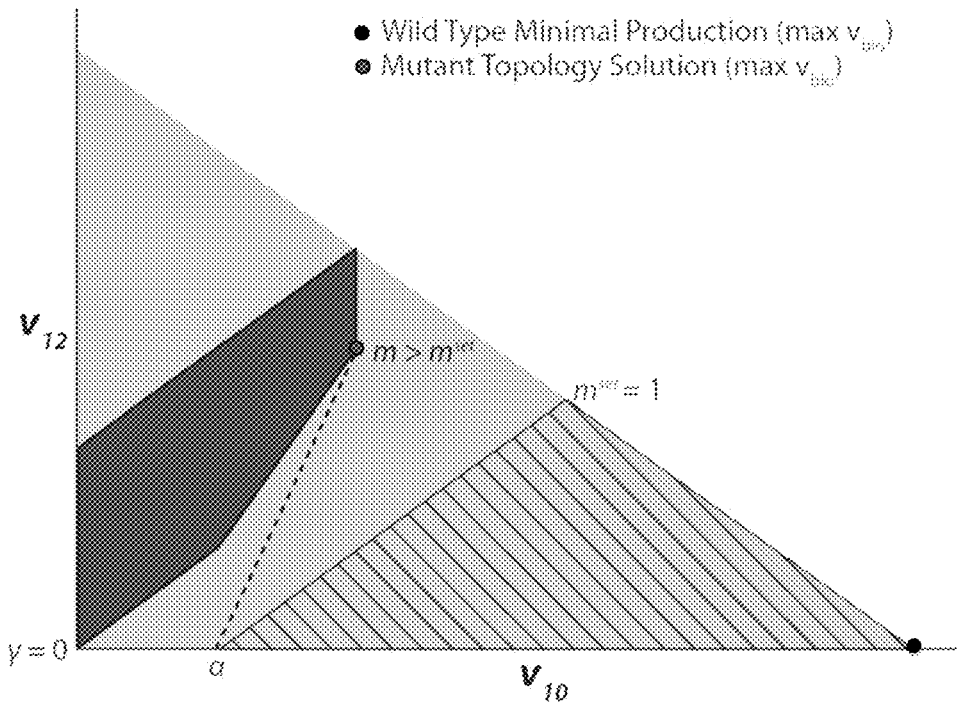

To demonstrate how the direct constraint module works, an illustrative example is provided in FIGS. 7A-7C. In this example, the direct constraint module is applied to ensure that beyond a given production of $E_{ex}$ there will be equivalent or greater production of $I_{ex}$, effectively forcing co-production of two compounds. This type of module could be used when the proposed strain needs to generate two products or co-utilize two substrates. To force such a mutant to be proposed by OptORF, we defined a point on the x-axis of the $v_{10}$-$v_{12}$ sub-space, ($\alpha$,0), and used a slope acceptance criterion of $m^{set}=1$. The resulting strain design is an interesting triple knockout mutant (missing fluxes $v_5$, $v_{11}$, and $v_{15}$) where maximal cellular growth requires both $E_{ex}$ and $I_{ex}$ production. In this case, deletion of $v_{15}$ ensures that production of $E_{ex}$ generates one or two molecules of C from $B_{ex}$ or $A_{ex}$, respectively. The C molecules produced can only be converted into biomass with $I_{ex}$ as a by-product when $v_5$ and $v_{11}$ are deleted. Thus, an ideal strain is created such that the cell's biological imperative is coupled to the co-production of two chemicals. The feasible region for the mutant is shown in FIGS. 7B and 7C.

Application of FaceCon Modules to a Genome-Scale *Escherichia coli* Model

Figure 8A:
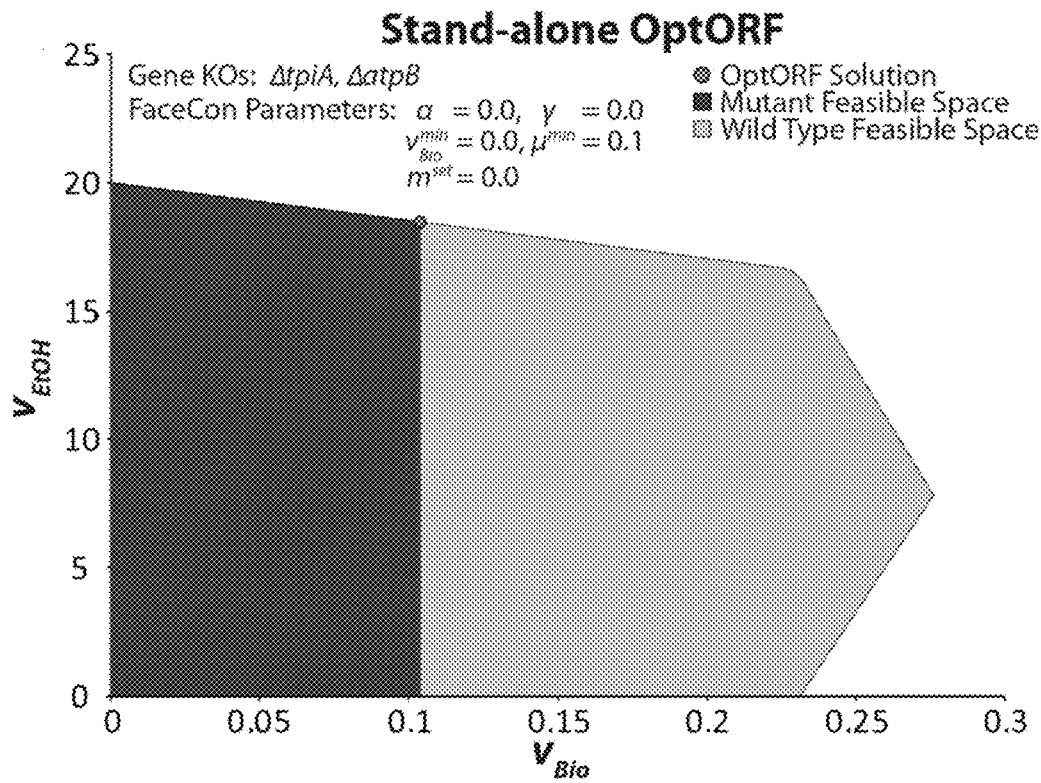
FIGS. 8A-D. Application of FaceCon to *E. coli* iJO1366 for production of ethanol.
Figure 8B:
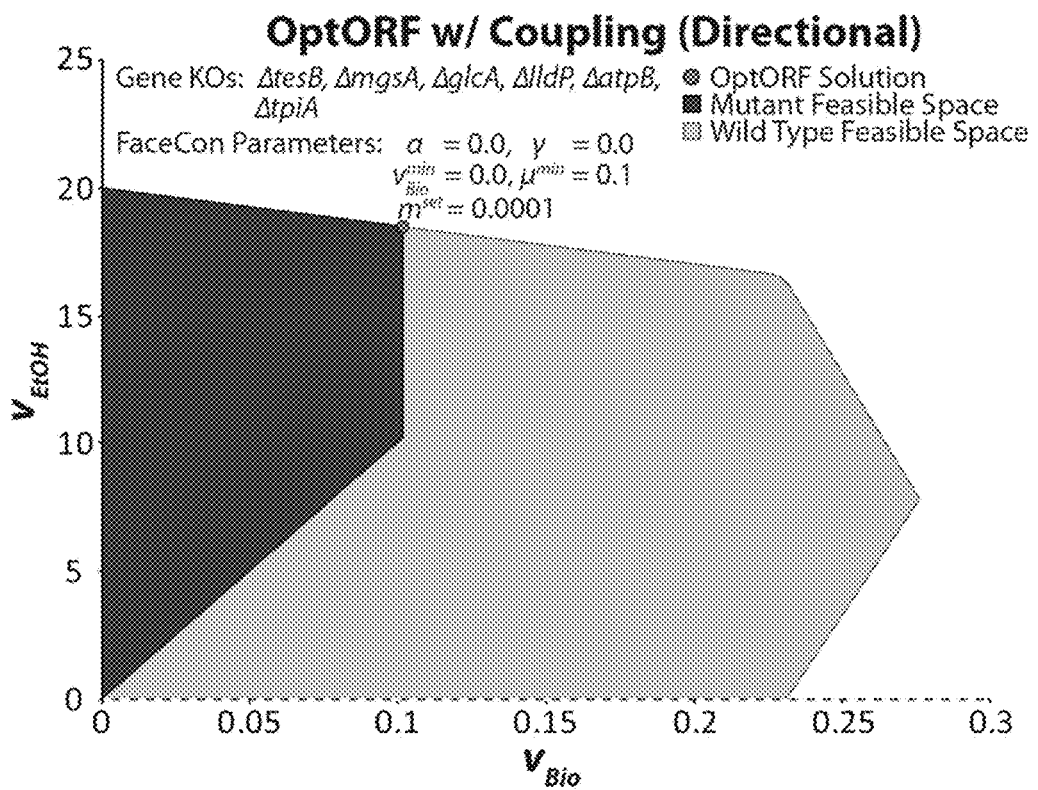
Figure 8C:
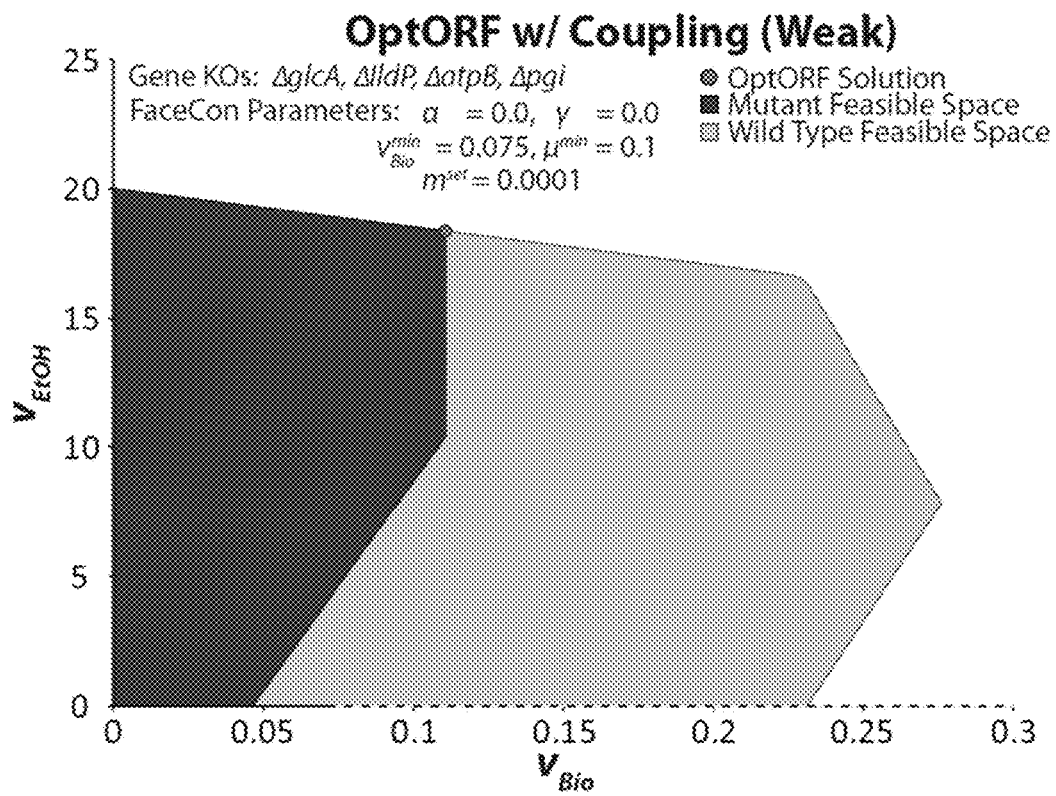
Figure 8D:
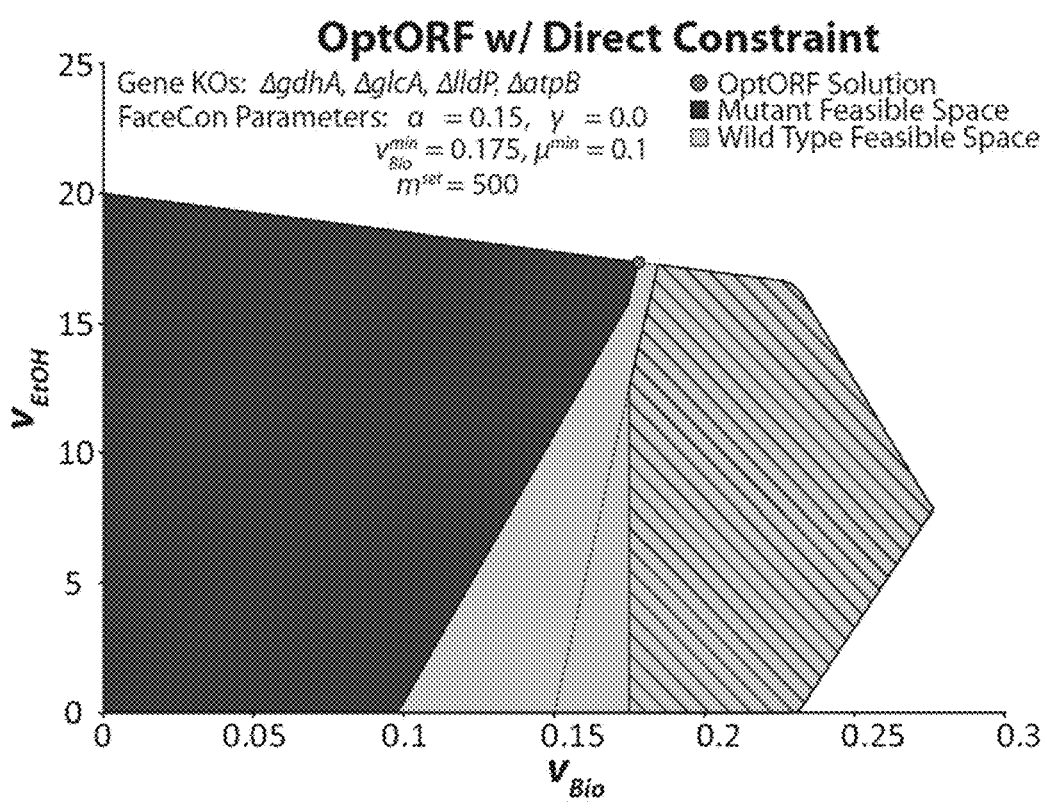
Figure 9A:
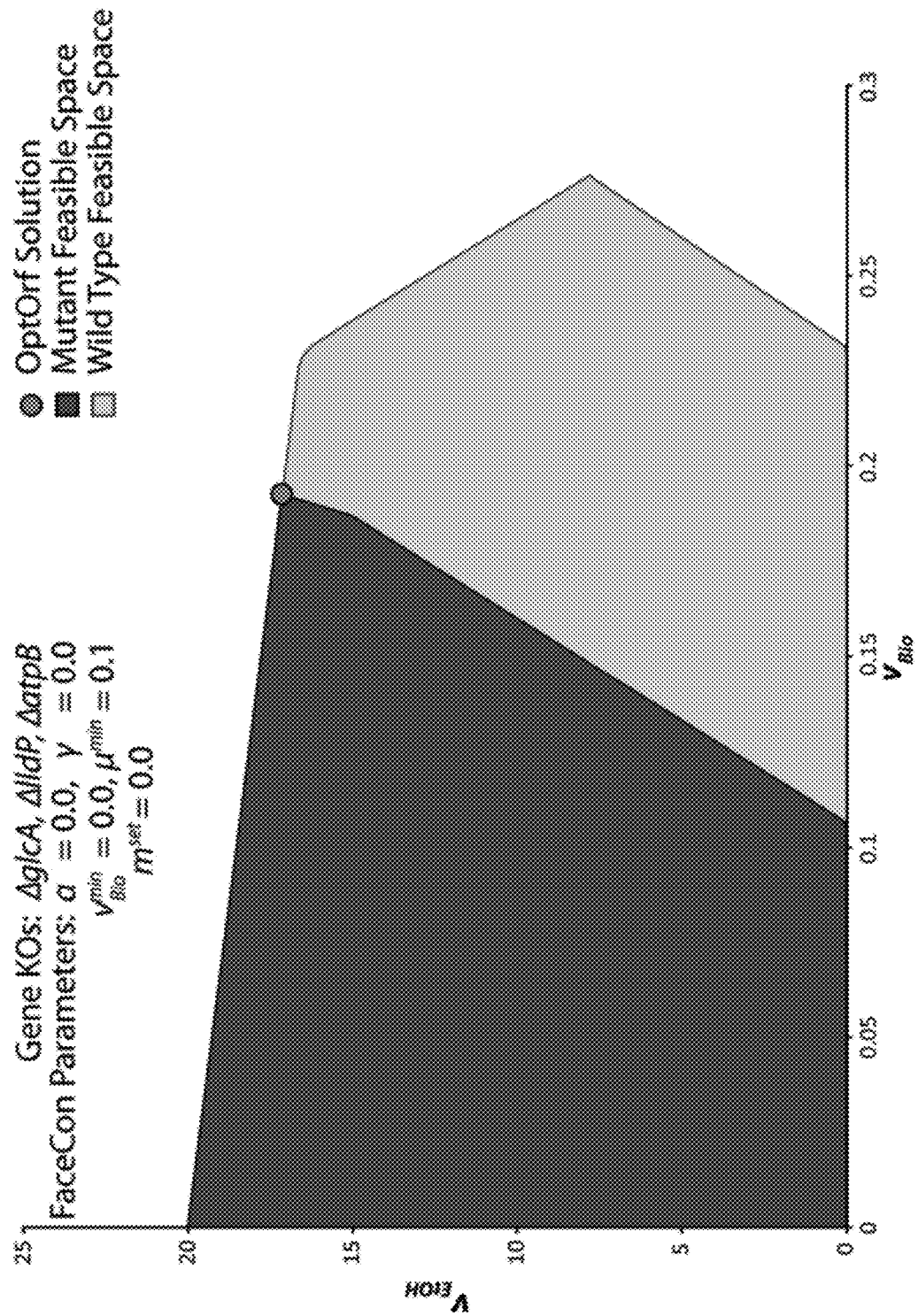
Figure 9C:
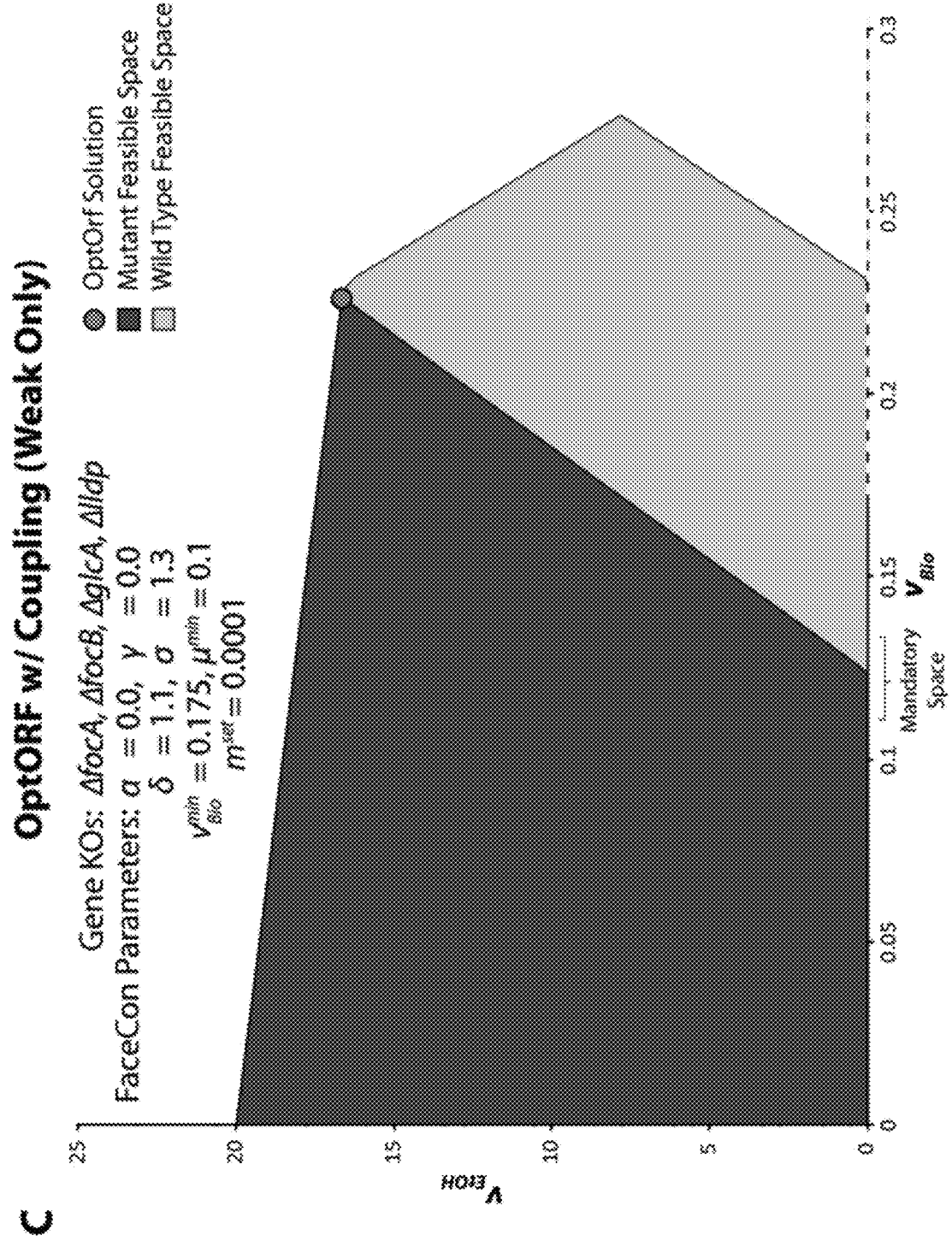
Figure 10A:
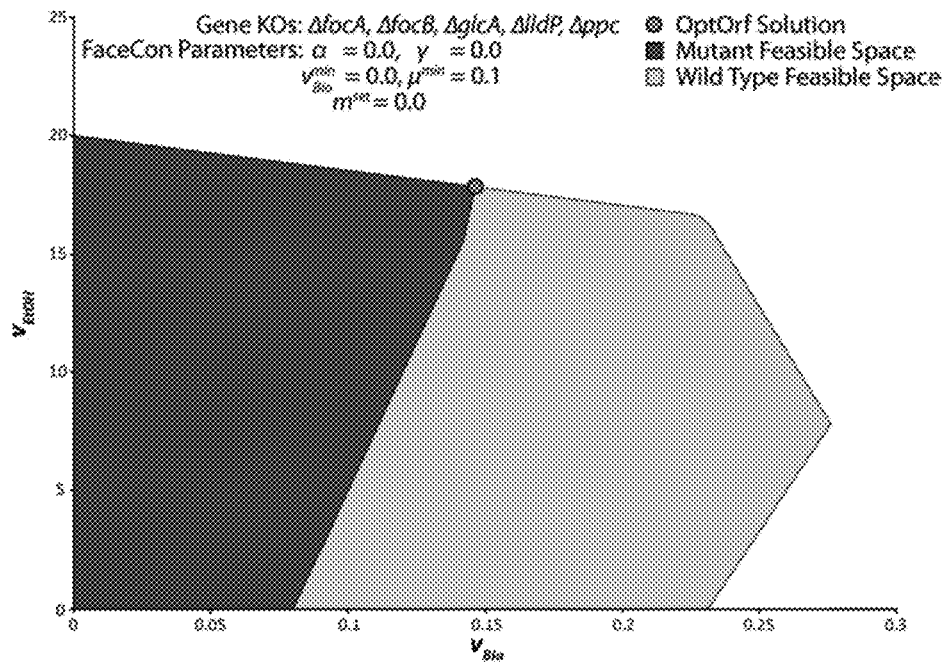
FIGS. 10A and 10B. Hypothetical by-product elimination in iJO1366. FaceCon constraints were added with OptORF so that any proposal must completely remove formate acid production functionality from iJO1366.
Figure 10B:
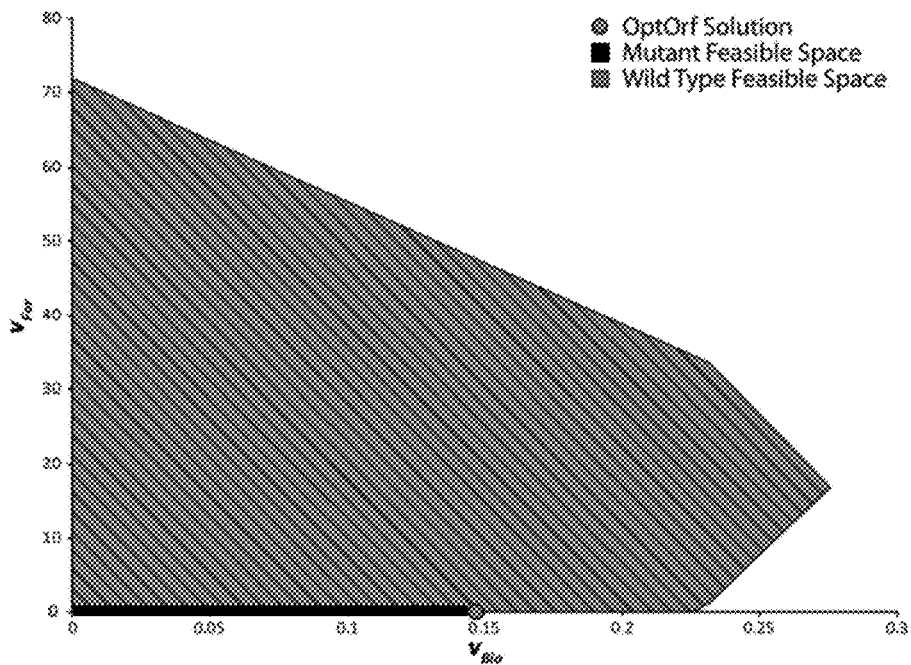
Figure 11:
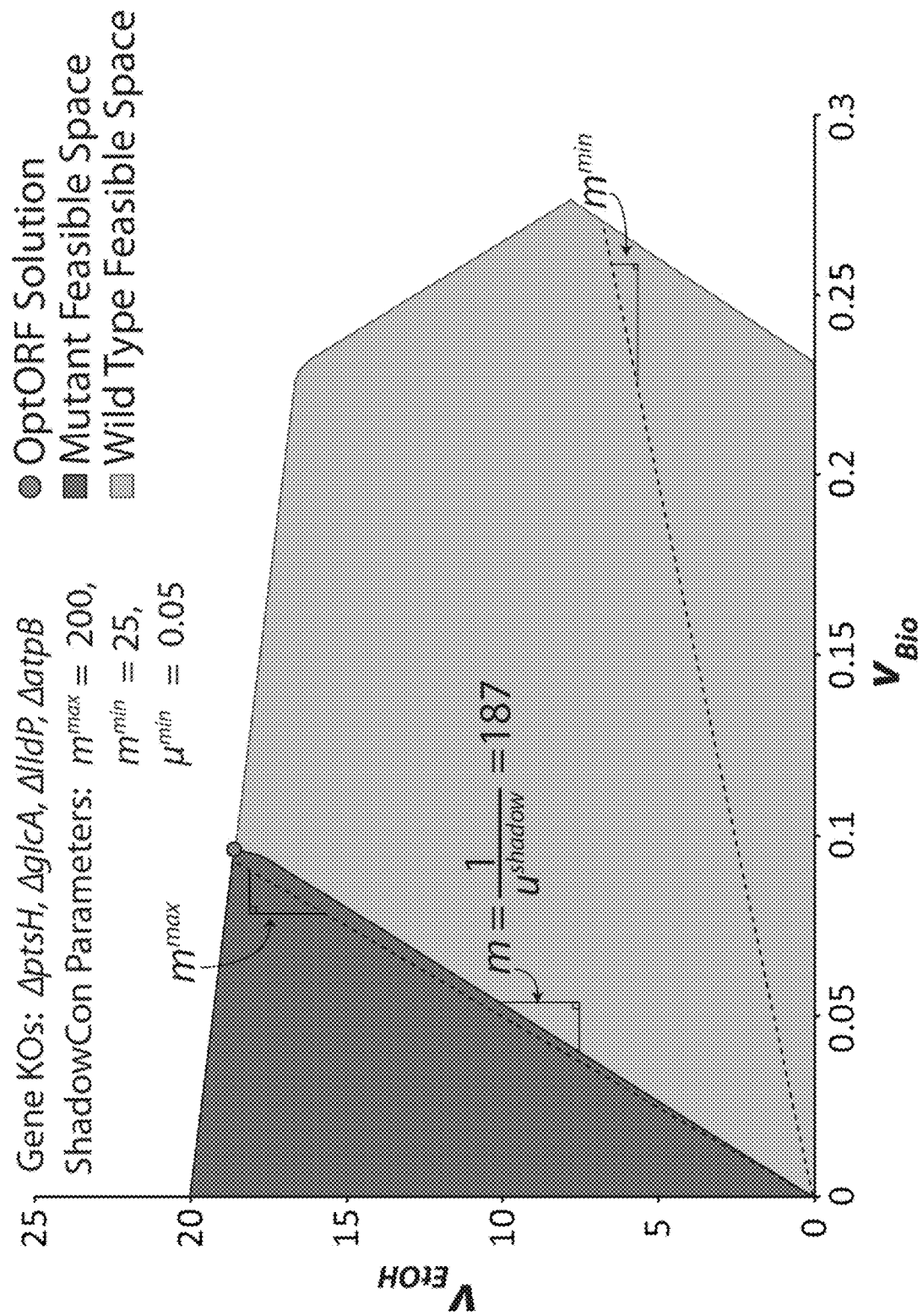
FIG. 11. Application of ShadowCon module to physiological functions in iJO1366. In this case, the ShadowCon module works to limit the slope of the line at the onset of coupling between ethanol and biomass production. Using the dual variable, $u^{shadow}$, associated with this line it is possible to constrain the slope, m, between a user-specified upper ($m^{max}$) and lower ($m^{min}$) bound (dashed lines).

To demonstrate the scalability of FaceCon modules to genome-scale problems, we applied OptORF in conjunction with FaceCon modules to design strains for anaerobic ethanol production from glucose in *E. coli* using the iJO1366 model [35]. A maximum glucose uptake rate (GUR) of 10 mmol/gDW/h was used. FIGS. 8B-8D show the different strain designs and solution space topologies that can be generated using FaceCon modules without needing to exhaustively query the set of stand-alone OptORF (OptORF without any FaceCon modules) solutions using integer cuts. As a baseline, we first show a stand-alone OptORF strain design's feasible region (FIG. 8A). While we did not use a tilted objective function [19] for the solutions provided in FIGS. 8B-D and FIG. 11, this can easily be incorporated into OptORF with a FaceCon module (see FIGS. 9A-10B for tilted solutions).

Since no tilt or maximum modification was added to OptORF [19, 33], the double knockout mutant (ΔtpiA ΔatpB) proposed by OptORF can have different amounts of ethanol production at the maximum growth rate (including no production), resulting in no coupling between biomass and ethanol production (ethanol production ranges between 0 and ~18.5 mmol/gDW/h at the maximum growth rate). This lack of coupling is because lactate can be produced as an alternative to ethanol during maximum growth. All the knockouts that are shown in FIGS. 8A-D secrete ethanol as a way to recycle NADH and NADPH anaerobically. Under fermentation conditions too many protons are generated internally and so ATP synthase operates in reverse, translocating protons from inside to outside the cell. Consequently, deleting ATP synthase (any one or more of atpA, atpB, atpC, aptD, atpE, atpF, atpG, and atpH), which appears in all solutions in FIGS. 8A-D and FIG. 11, forces the model to find alternate ways of dissipating intracellular protons. Converting pyruvate into ethanol or lactate consumes one cytoplasmic proton per NADH recycled, while an alternative path for consuming NADPH converts carbon dioxide into formate (using pyruvate formate lyase, pyruvate synthase, and flavodoxin reductase) and does not consume any cytoplasmic protons in the process. Consequently, the atpB deletion blocks this formate production pathway at the maximum growth rate and increases ethanol or lactate production so that more intracellular protons are incorporated into secreted products (ethanol or lactate). Deleting triose-phosphate isomerase (tpi) pushes flux through the Entner-Doudoroff pathway (instead of glycolysis), reducing ATP yields from glucose and thereby enhancing ethanol production by reducing maximum growth rates.

We next used a coupling module to generate a strain where there is always directional coupling between ethanol and biomass production (i.e., coupling module set strictly for directional coupling). To accomplish this, the minimal slope of a line in the feasible region going through the origin is calculated and a positive slope is required for acceptance. The feasible region for the resulting six gene deletion mutant is provided in FIG. 8B. This mutant also includes the tpiA and atpB knockouts, but also has deletions to remove alternative pathways for recycling NAD(P)H. The glcA and lldP knockouts prevents lactate production (which can also be accomplished by deleting the lactate dehydrogenases, dld and ldhA—an alternative solution), while the mgsA knockout, which codes for methylglyoxal synthase, prevents dihydroxyacetone from being converted to and secreted as (R)-1,2-Propanediol. The final knockout of tesB, a fatty-acid CoA thioesterase, prevents flux through 3-hydroxyacyl-CoA dehydrogenase and acyl-CoA dehydrogenase, and secretion of fatty acids (e.g., hexanoate) which consumes reductant. At maximum growth, the model predicts that some L-valine can be produced instead of ethanol and thus there remains a range for ethanol production (between ~10.2 and ~18.5 mmol/gDW/h).

While the fully coupled phenotype may be ideal (since any growth requires ethanol production), the mutant requires numerous deletions and may initially be sickly. To relax the design criteria, we found a weakly coupled strain where growth and ethanol production are coupled when $v_{Bio}$ is greater than $0.075$ $h^{-1}$. The four gene knockout mutant proposed (FIG. 8C) would be genetically simpler to construct and, while the selective pressure is not as strong as for the directionally coupled mutant, the ethanol production rates after adaptive evolution should be nearly equivalent (between ~10.4 and ~18.4 mmol/gDW/h). While this mutant also includes the atpB, glcA and lldP knockouts from the directionally coupled case, interestingly, this mutant uses the pgi (phosphoglucose isomerase) deletion (instead of tpi) to favor the Entner-Duodoroff pathway over glycolysis.

To demonstrate use of a direct constraint module, we created an excluded region where ethanol produced per unit additional biomass must be greater than 500 mmol ethanol/gDW (calculated from the point $\alpha=0.15$ $hr^{-1}$) for cells growing above $0.175$ $hr^{-1}$. Note, these parameters would ensure the designed mutant would have a minimum substrate-specific productivity [9] (calculated as $m^{set} \cdot (v_{Bio}^{min} \cdot (v_{bio}^{min}-\alpha))/GUR$), of at least ~0.22 mmol ethanol/mmol glucose/h for growth rates above $0.175$ $hr^{-1}$. Using this module, the four gene knockouts proposed (FIG. 8D) by OptORF achieved weak coupling between ethanol and biomass production and met the stated criteria. Unlike the previous solutions, this mutant would use glycolysis to achieve maximum growth. In this case, deleting gdhA (encoding glutamate dehydrogenase) forces glutamate to be produced using a less energy efficient pathway (involving glutamine synthetase and glutamate synthase, which consumes one additional ATP per glutamate synthesized). This reduces the maximum growth rate, such that the design criteria is satisfied. At the maximum growth rate, ethanol production is predicted to be ~17.4 mmol/gDW/h for this mutant.

In the previous examples, we selected feasible space constraints that restrict the ethanol production-cellular growth subspace; however, feasible space constraints can be used on other subspaces. We investigated the use of FaceCon modules for eliminating undesirable by-products, such as, succinate, acetate, and formate. A preliminary analysis indicated that under anaerobic conditions some baseline level of succinate secretion is required for cellular growth. Acetate secretion is not essential for growth but one or more acetate producing enzymes are essential for growth. Since there is no gene assigned to the acetate transport reaction there is no genetic way to eliminate acetate secretion. Consequently, we focused on finding a solution that could eliminate formate production at all growth rates and maximize ethanol production at the maximum growth rate (see FIGS. 10A and 10B). This five gene deletion strategy knocks out transporters for lactate (glcA and lldP—an alternate solution could instead delete the lactate dehydrogenases, ldhA and dld) and formate (focA and focB). In addition, deleting ppc (which encodes for phosphoenolpyruvate carboxylase) increases flux through malate synthase and malate dehydrogenase—generating more NADH to produce oxaloacetate—and decreases the maximum growth rate. As a result, the ppc deletion requires additional ethanol production to balance the newly generated reductant. The predicted ethanol production for this mutant at the maximum growth rate is ~17.8 mmol/gDW/h.

These examples show that FaceCon modules are both tractable at the genome-scale and can aid OptORF in proposing interesting mutants which meet multiple design criteria, with minimal impacts on production of the chemical of interest. These solutions would not be easily obtained using stand-alone OptORF. To find the mutants that satisfy these additional design criteria (FIGS. 8B-8D) using stand-alone OptORF would require numerous integer cuts due to the large number of gene deletions required to produce these phenotypes and the gene deletion penalty used by OptORF. For example, using stand-alone OptORF with integer cuts took ~13.4 hours to generate ten alternate solutions (the last four solutions alone took 11.1 hours). None of the ten proposed solutions satisfy the design criteria of the FaceCon solutions shown in FIGS. 8B-8D. In contrast, using OptORF in conjunction with FaceCon modules, desired solutions could be found directly, in a short amount of time (~2.8 hours). In addition, all of the OptORF with FaceCon strategies have very similar levels of maximum ethanol production (at the maximum growth rate) as the best solution found by stand-alone OptORF.

Previous computational studies have identified strategies for improving ethanol production in *E. coli* using constraint-based models. Trinh et al. previously used elementary mode analysis to design an eight gene deletion strain of *E. coli* (Δndh Δzwf ΔfrdA ΔsfcA ΔmaeB ΔldhA ΔpoxB Δpta) with high ethanol yields [25]. The OptORF with FaceCon strategies suggested in FIGS. 8B-8D required fewer mutations and are predicted to achieve higher ethanol yields at maximum cell growth; however, the Trinh et al. strains do guarantee a minimum yield 0.36 g ethanol/g glucose for all growth rates. Previously, OptORF was applied to an earlier metabolic model (iJR904) and eleven mutations were frequently suggested to improve ethanol production (appearing in at least 10% of 200 suggested strategies): ptsH, pgi, pflAB, pflCD, tdcE, tpi, pta, eutD, gdhA, gnd and nuoN [5]. These genes differ from those commonly found in OptORF with FaceCon strategies, which include atpB, glcA, and lldP (or equivalently atpB, dld, and ldhA). While differences in strain designs could be due to differences in the metabolic networks, this work suggests new strategies for improving ethanol production.

Shadow Price Constraint (ShadowCon) Module

While various methods such as 'tilting' the objective function, using a maximum problem, or adding FaceCon modules can ensure that growth and chemical production are coupled, none of these methods allow direct control or optimization of the ratio of $\Delta v_y/\Delta v_x$ at the onset of coupling between two fluxes, $v_x$ and $v_y$, thus defining the degree to which two fluxes are coupled. However, such a module can be designed by taking advantage of shadow prices in the dual of a flux balance analysis (FBA) problem. The FBA problem is formulated by adding an equality constraint for $v_y$ equal to ε (e.g., chemical production rate) to the standard set of FBA constraints and then maximizing $v_x$ (e.g., biomass production). In this case, the shadow price for the added equality constraint ($u^{shadow}$) indicates how $v_x$ changes for small changes in $v_y$ and is the inverse of the coupling line's slope since the shadow price is calculated near where coupling initially occurs on the x-axis (within some user-defined ε). By setting criteria for the shadow price associated with the added equality constraint, one can effectively control the degree of coupling between the two fluxes of interest (see below for additional details). The shadow price constraints module (ShadowCon) includes the FBA problem (described above), its dual formulation and additional constraints on the equality constraint's dual variable. Addition of ShadowCon to a strain design algorithm, especially in conjunction with other FaceCon modules, allows for greater control over the strength of the selective pressure for producing a given chemical or catalyzing a reaction of interest.

Application of ShadowCon Module to a Genome-Scale *Escherichia coli* Model

As a demonstration of how the ShadowCon module works, we have applied ShadowCon to iJO1366 (FIG. 11) requiring that the slope of the initial coupling line, m, fall between 25 and 200 mmol/gDW. This range was chosen to create a strong coupling between ethanol and biomass production while also preventing strategies from being proposed where no coupling exists. The resulting mutant includes a new knockout, ptsH that encodes a component of the PTS transport system. Deletion of ptsH or other subunits of the PTS transport system (ptsI, ptsG, and crr) forces glucose to be transported using either a proton symporter or ABC transporter, both of which produce a cytoplasmic proton. The additional proton reduces the growth rate and increases the maximum amount of ethanol produced (a ΔatpBΔglcAΔlldP mutant also satisfies the slope criteria but has a lower maximum ethanol production). In order to evaluate the sensitivity of ethanol production (at the maximum growth rate) to the coupling line's slope, we ran OptORF with the ShadowCon module using increasingly more stringent slope requirements. In this case, a tilted objective was used (see methods for details) and the lower bound on the slope was increased from 25 until the ShadowCon module prevented finding an OptORF solution (see Table 2). As can be seen, the OptORF chemical production objective is eventually sensitive to increasing slope requirements; however, the predicted production is still sufficiently high for a wide range of slopes.

TABLE 2

Sensitivity of mutant proposals and chemical production to $m^{min}$ changes using tilted OptORF.

| $m^{min}$-$m^{max}$ (mmol Ethanol/ gDW) | Knockouts | m (mmol Ethanol/ gDW) | Max Ethanol Production (mmol/ gDW/h)[#] | Min Ethanol Production (mmol/ gDW/h) |
|---|---|---|---|---|
| 800-1000 | ydbK, gdhA, tpiA, ppc | 843 | 10.02 | 10.02 |
| 600-1000 | tpiA, fpr, ppc | 753 | 10.03 | 10.03 |
| 400-1000 | tpiA, fpr, ppc | 753 | 10.03 | 10.03 |
| 200-1000 | glcA, lldP, atpB, ppc | 278 | 18.07 | 18.07 |
| 25-1000 | glcA, lldP, atpB | 187 | 17.15 | 17.15 |

[#]The OptORF outer objective function maximizes the maximum ethanol product rate minus the total number of gene knockouts; however, isozymes (e.g. glcA and lldP) were counted as one gene knockout since all but one isozyme were deleted from the model to reduce the number of decision variables.

Figure 12:
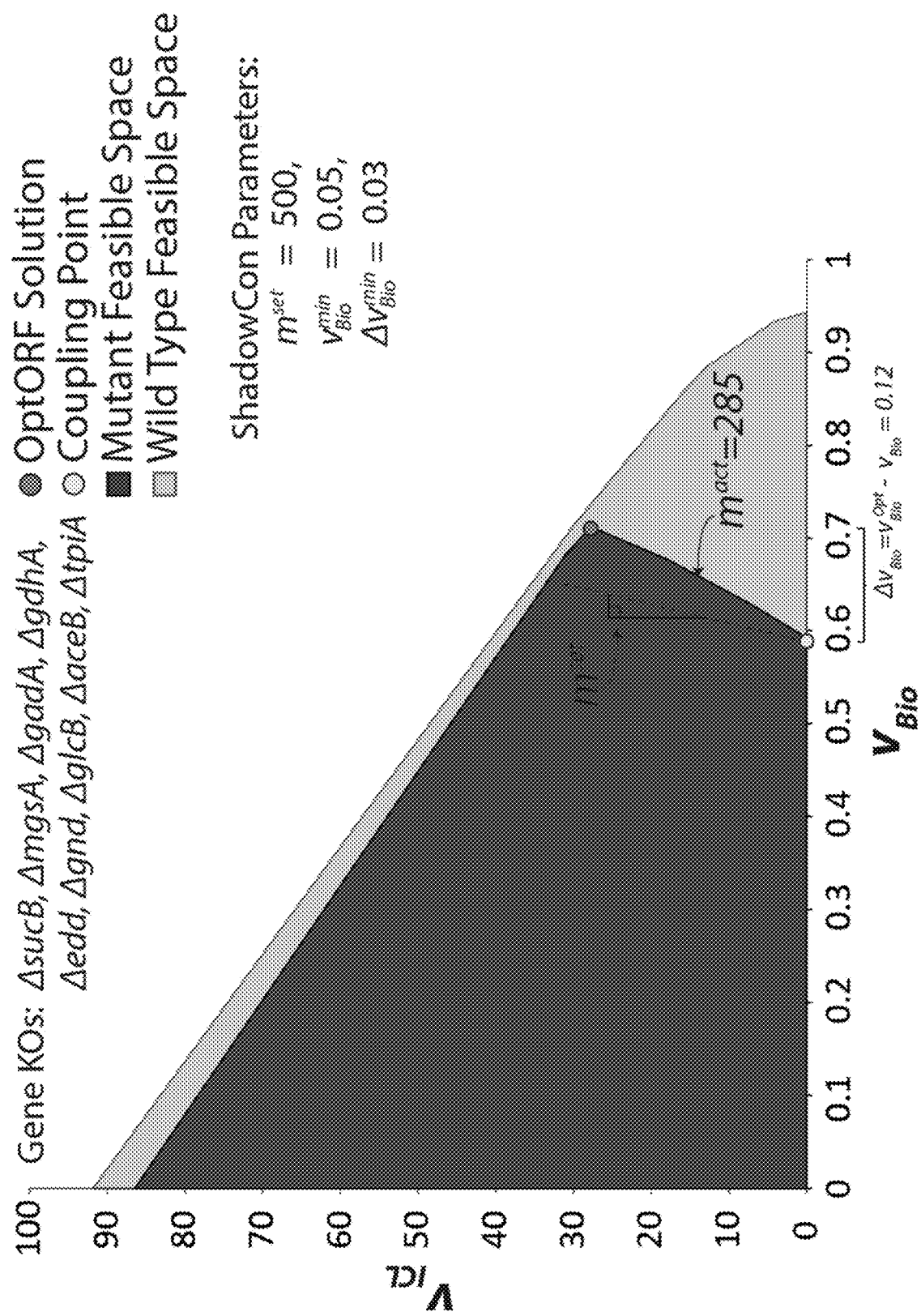
FIG. 12. Application of ShadowCon module to metabolic functions in iJO1366. In this case, the ShadowCon module works to optimize the slope of the line at the onset of coupling between isocitrate lyase (ICL) and biomass production. Using the dual variable, $u^{shadow}$, associated with this line it is possible to optimize the slope, m, to be close to a desired value ($m^{set}$). The actual slope of the mutant ($m^{act}$) also shown. The additional constraints imposed are also listed in the figure and their impact is discussed more thoroughly in the methods section of the Examples.

As another example, we applied ShadowCon to identify mutants with a desired coupling between biomass production and a desired metabolic function. In this case the desired enzymatic activity was isocitrate lyase (ICL), an enzyme that is not predicted to be used during maximal aerobic growth on glucose minimal media (FIG. 12). The desired slope between ICL and biomass fluxes ($m^{set}$) was set to 500, and the slope of the identified mutant was 285. The identified mutant included 9 gene deletions (sucB, mgsA, gadA, gdhA, edd, gnd, glcB, aceB, and tpiA) and its solution space is shown in FIG. 12. This example illustrates that ShadowCon modules can not only limit the slope at which coupling occurs, but can also try and find slopes near desired values. Furthermore, this example illustrates that ShadowCon modules can be used to identify deletions to enhance not just biochemical production but also flux through desired reactions. The ShadowCon solution describes genetic conditions where adaptive evolution of the resulting mutant could lead to enhanced catalytic activities of the desired metabolic function (in this case isocitrate lyase).

CONCLUSIONS

We have developed FaceCon and ShadowCon modules to extend upon the capabilities of existing mixed integer linear adaptive evolution metabolic engineering algorithms. Future work, could involve incorporating these methods into other types of metabolic engineering algorithms. Nonetheless, we show such modules are applicable to genome-scale models as shown using the *E. coli* model iJO1366. Using these modules will allow greater control over the knockout strategies proposed and allow for more efficient generation of phenotypes of interest, including complex phenotypes that would be difficult, if not impossible, to find using existing metabolic engineering algorithms alone. Moreover, using these approaches could allow for parallelization of metabolic engineering algorithms by starting multiple runs simultaneously with different FaceCon or ShadowCon parameters. Such an approach would result in more diverse and interesting solutions and could save additional time over sequential approaches for multiple solutions which rely on integer cuts. Using FaceCon and ShadowCon modules in conjunction with one another will allow researchers to define multiple engineering design criteria that should be met by any strain proposed. Through our illustrative and genome-scale examples, we have touched upon a number of possible applications for FaceCon modules such as by-product inhibition, coupling constraints, and co-production of metabolites. Another possible use may include constraining chemical production with increasing carbon uptake. Using these modular approaches, we hope to provide algorithm flexibility so that researchers have fewer limitations when using their strain design algorithm.

REFERENCES

1. Orth J D, Thiele I, Palsson B O (2010) What is flux balance analysis? Nat Biotech 28: 245-248.
2. Curran K A, Alper H S (2012) Expanding the chemical palate of cells by combining systems biology and metabolic engineering. Metabolic Engineering 14: 289-297.
3. Zomorrodi A R, Suthers P F, Ranganathan S, Maranas C D (2012) Mathematical optimization applications in metabolic networks. Metabolic Engineering 14: 672-686.
4. Lee J W, Na D, Park J M, Lee J, Choi S, et al. (2012) Systems metabolic engineering of microorganisms for natural and non-natural chemicals. Nat Chem Biol 8: 536-546.
5. Kim J, Reed J (2010) OptORF: Optimal metabolic and regulatory perturbations for metabolic engineering of microbial strains. BMC Systems Biology 4: 53.
6. Burgard A P, Pharkya P, Maranas C D (2003) Optknock: A bilevel programming framework for identifying gene knockout strategies for microbial strain optimization. Biotechnology and Bioengineering 84: 647-657.
7. Pharkya P, Burgard A P, Maranas C D (2004) OptStrain: A computational framework for redesign of microbial production systems. Genome Research 14: 2367-2376.
8. Ranganathan S, Suthers P F, Maranas C D (2010) OptForce: An Optimization Procedure for Identifying All Genetic Manipulations Leading to Targeted Overproductions. PLoS Comput Biol 6: e1000744.
9. Patil K, Rocha I, Forster J, Nielsen J (2005) Evolutionary programming as a platform for in silico metabolic engineering. BMC Bioinformatics 6: 308.
10. Pharkya P, Maranas C D (2006) An optimization framework for identifying reaction activation/inhibition or elimination candidates for overproduction in microbial systems. Metabolic Engineering 8: 1-13.
11. Cotten C, Reed J L (2013) Constraint-based strain design using continuous modifications (CosMos) of flux bounds finds new strategies for metabolic engineering. Biotechnology Journal 8: 595-604.
12. Choi H S, Lee S Y, Kim T Y, Woo H M (2010) In Silico Identification of Gene Amplification Targets for Improvement of Lycopene Production. Applied and Environmental Microbiology 76: 3097-3105.
13. Kim J, Reed J L, Maravelias C T (2011) Large-Scale Bi-Level Strain Design Approaches and Mixed-Integer Programming Solution Techniques. PLoS ONE 6: e24162.
14. Ohno S, Shimizu H, Furusawa C (2013) FastPros: Screening of reaction knockout strategies for metabolic engineering. Bioinformatics.
15. Lun D S, Rockwell G, Guido N J, Baym M, Kelner J A, et al. (2009) Large-scale identification of genetic design strategies using local search. Molecular Systems Biology 5.
16. Yang L, Cluett W R, Mahadevan R (2011) EMILiO: A fast algorithm for genome-scale strain design. Metabolic Engineering 13: 272-281.
17. Fong S S, Burgard A P, Herring C D, Knight E M, Blattner F R, et al. (2005) In silico design and adaptive evolution of Escherichia coli for production of lactic acid. Biotechnology and Bioengineering 91: 643-648.
18. Yim H, Haselbeck R, Niu W, Pujol-Baxley C, Burgard A, et al. (2011) Metabolic engineering of Escherichia coli for direct production of 1,4-butanediol. Nat Chem Biol 7: 445-452.
19. Feist A M, Zielinski D C, Orth J D, Schellenberger J, Herrgard M J, et al. (2010) Model-driven evaluation of the production potential for growth-coupled products of Escherichia coli. Metabolic Engineering 12: 173-186.
20. Lin H, Bennett G N, San K-Y (2005) Metabolic engineering of aerobic succinate production systems in Escherichia coli to improve process productivity and achieve the maximum theoretical succinate yield. Metabolic Engineering 7: 116-127.
21. Sánchez A M, Bennett G N, San K-Y (2005) Novel pathway engineering design of the anaerobic central metabolic pathway in Escherichia coli to increase succinate yield and productivity. Metabolic Engineering 7: 229-239.
22. Vadali R V, Fu Y, Bennett G N, San K-Y (2005) Enhanced Lycopene Productivity by Manipulation of Carbon Flow to Isopentenyl Diphosphate in Escherichia coli. Biotechnology Progress 21: 1558-1561.
23. Gawand P, Hyland P, Ekins A, Martin V J J, Mahadevan R (2013) Novel approach to engineer strains for simultaneous sugar utilization. Metabolic Engineering 20: 63-72.
24. Lian J, Chao R, Zhao H (2014) Metabolic engineering of a Saccharomyces cerevisiae strain capable of simultaneously utilizing glucose and galactose to produce enantiopure (2R,3R)-butanediol. Metabolic Engineering 23: 92-99.
25. Trinh C T, Unrean P, Srienc F (2008) Minimal Escherichia coli Cell for the Most Efficient Production of Ethanol from Hexoses and Pentoses. Applied and Environmental Microbiology 74: 3634-3643.
26. Aristidou A A, San K-Y, Bennett G N (1994) Modification of central metabolic pathway in Escherichia coli to reduce acetate accumulation by heterologous expression of the Bacillus subtilis acetolactate synthase gene. Biotechnology and Bioengineering 44: 944-951.
27. Eiteman M A, Altman E (2006) Overcoming acetate in Escherichia coli recombinant protein fermentations. Trends in Biotechnology 24: 530-536.
28. Jantama K, Zhang X, Moore J C, Shanmugam K T, Svoronos S A, et al. (2008) Eliminating side products and increasing succinate yields in engineered strains of Escherichia coli C. Biotechnology and Bioengineering 101: 881-893.
29. Zha W, Rubin-Pitel S B, Shao Z, Zhao H (2009) Improving cellular malonyl-CoA level in Escherichia coli via metabolic engineering. Metabolic Engineering 11: 192-198.
30. Hädicke O, Klamt S (2011) Computing complex metabolic intervention strategies using constrained minimal cut sets. Metabolic Engineering 13: 204-213.
31. von Kamp A, Klamt S (2014) Enumeration of Smallest Intervention Strategies in Genome-Scale Metabolic Networks. PLoS Comput Biol 10: e1003378.
32. Tervo C, Reed J (2012) FOCAL: an experimental design tool for systematizing metabolic discoveries and model development. Genome Biology 13: R116.
33. Tepper N, Shlomi T (2010) Predicting metabolic engineering knockout strategies for chemical production: accounting for competing pathways. Bioinformatics 26: 536-543.

34. Burgard A P, Nikolaev E V, Schilling C H, Maranas C D (2004) Flux Coupling Analysis of Genome-Scale Metabolic Network Reconstructions. Genome Research 14: 301-312.
35. Orth J D, Conrad T M, Na J, Lerman J A, Nam H, et al. (2011) A comprehensive genome-scale reconstruction of *Escherichia coli* metabolism—2011. Mol Syst Biol 7.
36. Hamilton J J, Reed J L (2012) Identification of Functional Differences in Metabolic Networks Using Comparative Genomics and Constraint-Based Models. PLoS ONE 7: e34670.
37. Sierksma G (2002) Linear and Integer Programming: Theory and Practice. New York: Marcel Dekker, Inc.
38. Tervo C J, Reed J L. Expanding Metabolic Engineering Algorithms Using Feasible Space and Shadow Price Constraint Modules. Metab Eng Commun. 2014 Dec. 1; 1:1-11.

What is claimed is:

1. A method for identifying one or more modifications to a cell for performing a physiological function, the method comprising:
    predicting, as an inner problem of a metabolic engineering algorithm configured to identify modifications for eliciting at least a first criterion of the physiological function, the one or more modifications as capable of eliciting the first criterion of the physiological function in addition to at least one additional criterion of the physiological function, wherein each of the one or more modifications is selected from the group consisting of a gene deletion and a gene addition, wherein the cell is a cell having a characterized network map, and wherein the at least one additional criterion comprises at least one of additional criteria (1), (4), (5), and (6):
        (1) a first non-zero rate of flux through a second reaction in the network map implying a non-zero rate of flux through a first reaction in the network map if the first non-zero rate of flux through the second reaction is greater than a first user-defined second-reaction flux value, in combination with a second non-zero rate of flux through the second reaction implying a zero rate of flux through the first reaction if the second non-zero rate of flux through the second reaction equals a second user-defined second-reaction flux value that is greater than zero and less than the first user-defined second-reaction flux value, wherein the first reaction and the second reaction are different reactions;
        (4) a ratio of a change of rate of flux through a seventh reaction in the network map per a change of rate of flux through an eighth reaction in the network map being greater than a user-defined ratio of a change of rate of flux through the seventh reaction per a change of rate of flux through the eighth reaction at rates of flux through the eighth reaction greater than a user-defined eighth-reaction flux value, wherein the seventh reaction and the eighth reaction are different reactions;
        (5) a ratio of a change of rate of flux through a ninth reaction in the network map per a change of rate of flux through a tenth reaction in the network map being less than a user-defined ratio of a change of rate of flux through the ninth reaction per a change of rate of flux through the tenth reaction at rates of flux through the tenth reaction greater than a user-defined tenth-reaction flux value, wherein the ninth reaction and the tenth reaction are different reactions; and
        (6) a ratio of a change of rate of flux through an eleventh reaction in the network map per a change of rate of maximal flux through a twelfth reaction in the network map being between user-specified values or being maximized or minimized, wherein the eleventh reaction and the twelfth reaction are different reactions; and
    modifying the cell to have the one or more modifications.

2. The method of claim 1, wherein a reaction selected from the group consisting of the first reaction, the seventh reaction, and the eleventh reaction comprises extracellular production of a desired compound and/or a desired enzyme activity.

3. The method of claim 1, wherein the ninth reaction comprises extracellular production of an undesired compound and/or an undesired enzyme activity.

4. The method of claim 1, wherein a reaction selected from the group consisting of the second reaction, the eighth reaction, the tenth reaction, and the twelfth reaction comprises biomass production.

5. The method of claim 1, wherein the at least one additional criterion comprises at least two of additional criteria (1), (4), and (6), and wherein two or more reactions selected from the group consisting of the first reaction, the seventh reaction, and the eleventh reaction comprises extracellular production of a same compound.

6. The method of claim 1, wherein the physiological function comprises increased or decreased production of a compound.

7. The method of claim 6, wherein a reaction selected from the group consisting of the first reaction, the seventh reaction, and the eleventh reaction comprises production of the compound.

8. The method of claim 1, wherein the physiological function comprises an increase or decrease in activity of one or more enzymes.

9. The method of claim 1, wherein the cell is a microorganism.

10. The method of claim 1, wherein the first criterion is producing a chemical at a specified level at a specified cell growth rate.

11. The method of claim 1, wherein the first criterion is maximizing chemical production at a maximal cell growth rate.

12. The method of claim 1, wherein the at least one additional criterion comprises at least additional criterion (1).

13. The method of claim 1, wherein the at least one additional criterion further comprises additional criterion (2):
    (2) each rate of flux through a third reaction in the network map being greater than a user-defined third-reaction flux value when the rate of flux through a fourth reaction in the network map is greater than a user-defined fourth-reaction flux value, wherein the third reaction and the fourth reaction are different reactions.

14. The method of claim 1, wherein the at least one additional criterion further comprises additional criterion (3):
    (3) each rate of flux through a fifth reaction in the network map being less than a user-defined fifth-reaction flux value when the rate of flux through a sixth reaction in the network map is greater than a user-defined sixth-reaction flux value, wherein the fifth reaction and the sixth reaction are different reactions.

15. The method of claim 1, wherein the at least one additional criterion comprises at least additional criterion (4).

16. The method of claim 1, wherein the at least one additional criterion comprises at least additional criterion (5).

17. The method of claim 1, wherein the at least one additional criterion comprises at least additional criterion (6).

18. The method of claim 1, wherein the at least one additional criterion comprises at least one of additional criteria (4), (5), and (6).

* * * * *